United States Patent
Karlovac et al.

(10) Patent No.: US 10,571,395 B2
(45) Date of Patent: Feb. 25, 2020

(54) UNIVERSAL RAPID DIAGNOSTIC TEST READER WITH TRANS-VISUAL SENSITIVITY

(71) Applicant: Holomic LLC, Los Angeles, CA (US)

(72) Inventors: Neven Karlovac, Pacific Palisades, CA (US); Onur Mudanyali, Cerritos, CA (US); Sophie Lorraine Gerrick, Los Angeles, CA (US); Ray Carlisle Delcher, Oxnard, CA (US); Derek Kuochao Tseng, Buena Park, CA (US)

(73) Assignee: NOWDiagnostics, Inc., Springdale, AR (US)

( * ) Notice: Subject to any disclaimer, the term of this patent is extended or adjusted under 35 U.S.C. 154(b) by 33 days.

(21) Appl. No.: 14/313,615

(22) Filed: Jun. 24, 2014

(65) Prior Publication Data

US 2015/0056719 A1 Feb. 26, 2015

Related U.S. Application Data

(60) Provisional application No. 61/899,116, filed on Nov. 1, 2013, provisional application No. 61/889,821, filed (Continued)

(51) Int. Cl.
*G01N 21/59* (2006.01)
*G01N 21/55* (2014.01)
(Continued)

(52) U.S. Cl.
CPC ............. *G01N 21/59* (2013.01); *G01N 21/55* (2013.01); *H04N 5/2354* (2013.01); *H04N 7/18* (2013.01);
(Continued)

(58) Field of Classification Search
CPC ........... G01N 2021/1765; G01N 21/55; G01N 21/59; G01N 21/8483; G01N 2201/062;
(Continued)

(56) References Cited

U.S. PATENT DOCUMENTS

| 8,947,656 B2 * | 2/2015 | Cunningham | ............ G01J 3/28 356/300 |
| 2006/0142947 A1 | 6/2006 | Robrish et al. | |

(Continued)

FOREIGN PATENT DOCUMENTS

| DE | 20 2012 101167 | 7/2013 |
| WO | WO 2009/063185 | 5/2009 |

(Continued)

OTHER PUBLICATIONS

Mudanyali "Integrated Rapid-diagnostic test reader platform on a cellphone" Lab Chip, 2012, 12,2678-2686.*

(Continued)

*Primary Examiner* — Samuel P Siefke
(74) *Attorney, Agent, or Firm* — Sandra Poteat Thompson; Finlayson Toffer Roosevelt & Lilly

(57) ABSTRACT

A universal rapid diagnostics test reader is disclosed and described herein that includes a set of control electronics, a digital camera component, an illumination component, a housing component, and a rapid diagnostics test tray, wherein the tray can hold at least one rapid diagnostics test having a shape and a size in a fixed position relative to the digital camera component and the illumination component, and wherein the reader can accommodate more than one different rapid diagnostics test. Methods are also disclosed that include: providing at least one first rapid diagnostics test having a first physical size, first feature and first format; providing at least one second rapid diagnostics test having a second physical size, second feature and second format;

(Continued)

inserting the first rapid diagnostics test in a universal rapid diagnostics test reader; analyzing the first rapid diagnostics test using the universal rapid diagnostics test reader; removing the first rapid diagnostics test from the reader; inserting the second rapid diagnostics test in a universal rapid diagnostics test reader without any mechanical adjustments of the reader or without the use of any additional parts or additional inserts; and analyzing the second rapid diagnostics test using the universal rapid diagnostics test reader.

22 Claims, 14 Drawing Sheets

Related U.S. Application Data on Oct. 11, 2013, provisional application No. 61/845,742, filed on Jul. 12, 2013.

(51) Int. Cl.
  *H04N 5/235* (2006.01)
  *H04N 7/18* (2006.01)
  *G01N 21/17* (2006.01)

(52) U.S. Cl.
  CPC ............... *G01N 2021/1765* (2013.01); *G01N 2201/062* (2013.01); *G01N 2201/125* (2013.01)

(58) Field of Classification Search
  CPC ...... G01N 2201/125; G01N 33/48785; H04M 1/72527; H04M 2250/52; H04N 5/2354; H04N 7/18
  See application file for complete search history.

(56) References Cited

U.S. PATENT DOCUMENTS

| | | | |
|---|---|---|---|
| 2006/0222567 A1* | 10/2006 | Kloepfer | G01N 21/78 422/68.1 |
| 2008/0038711 A1 | 2/2008 | Curry et al. | |
| 2010/0136521 A1 | 6/2010 | Yoon et al. | |
| 2010/0254581 A1 | 10/2010 | Neeser et al. | |
| 2010/0297659 A1 | 11/2010 | Yoo et al. | |
| 2013/0203043 A1* | 8/2013 | Ozcan | G06F 19/3487 435/5 |
| 2013/0244339 A1 | 9/2013 | Ehrenkranz et al. | |
| 2013/0273528 A1 | 10/2013 | Ehrenkranz | |
| 2014/0072189 A1* | 3/2014 | Jena | G01N 21/8483 382/128 |
| 2014/0170757 A1 | 6/2014 | Tsai | |
| 2014/0213468 A1 | 7/2014 | Ehrenkranz | |
| 2014/0375803 A1* | 12/2014 | Quilter | G01N 35/00871 348/143 |
| 2016/0327473 A1* | 11/2016 | Ozcan | G01N 33/1813 |

FOREIGN PATENT DOCUMENTS

| | | |
|---|---|---|
| WO | WO 2010/095394 | 8/2010 |
| WO | PCT/US2012/040282 | 5/2012 |
| WO | PCT/US2013/036446 | 4/2013 |

OTHER PUBLICATIONS

P. Yager, T. Edwards, E. Fu, K. Helton, K. Nelson, M. R. Tam and B. H. Weigl, Nature, 2006, 442, 412-418.
S. Banoo, D. Bell, P. Bossuyt, A. Herring, D. Mabey, et al., Nat Rev Microbio, 2006, 4, 21-31.
M. Dhorda, P. Piola, D. Nyehangane, B. Tumwebaze, A. Nalusaji, C. Nabasumba, E. Turyakira, R. McGready, E. Ashley, P. J. Guerin, G. Snounou, Am J Trop Med Hyg, 2012, 86(1), 93-95.
I. N. Okeke, R. W. Peeling, H. Goossens, R. Auckenthaler, S. S. Olmsted, J.F. de Lavison, B. L. Zimmer, M. D. Perkins, and K. Nordqvist, Drug Resist Updat, 2011, 14(2), 95-106.
C. Drakeley and H. Reyburn, Trans R Soc Trop Med Hyg, 2009, 103(4), 333-337.
C. K. Murray, R. A. Gasser Jr, A. J. Magill, and R.S. Miller, Clin Microbiol Rev, 2008, 21(1), 97-110.
J. Skarbinski, P. O. Ouma, L. M. Causer, S. K. Kariuki, J. W. Barnwell, J. A. Alaii, A. M. de Oliveira, D. Zurovac, B. A. Larson, R. W. Snow, A. K. Rowe, K. F. Laserson, W. S. Akhwale, L. Slutsker, and M. J. Hamel, Am J Trop Med Hyg, 2009, 80(6), 919-926.
L. A Mills, J. Kagaayi, J. P. Shoff, K. Newell, J. B. Bwanika, V. Ssempijja, S. Aluma, T.C. Quinn, S. J. Reynolds, R.H. Gray, Trans R Soc Trop Med Hyg, 2010, 104(3), 237-239.
http://www.itu.int/ITU-D/ict/publications/idi/material/2012/MIS2012_highlights_short.pdf.
H. Zhu, O. Yaglidere , T. Su , D. Tseng, and A. Ozcan, Lab Chip, 2011, 11, 315-322.
D. Tseng , O. Mudanyali , C. Oztoprak , S. O. Isikman , I. Sencan , O. Yaglidere, and A. Ozcan, Lab Chip, 2010, 10, 1787-1792.
O. Mudanyali , D. Tseng , C. Oh , S. O. Isikman , I. Sencan , W. Bishara , C. Oztoprak , S. Seo , B. Khademhosseini, and A. Ozcan, Lab Chip, 2010, 10, 1417-1428.
G. McKiernan, Searcher, 2010, 18 (3), 48-51.
A. W. Martinez, S. T. Philips, E. Carrilho, S. W. Thomas III, Hayat Sindi and G. M. Whitesides, Anal Chem, 2008, 80, 3699-3707.
Adler R., Health Care Unplugged: The Evolving Role of Wireless Technology, California HealthCare Foundation, 2007.
A. Coskun, J. Wong, D. Khodadadi, R. Nagi, A. Tey, and A. Ozcan, Lab Chip, 2012, DOI: 10.1039/C2LC41152K.
http://www.idc.com/getdoc.jsp?containerId=prUS23771812.
O. Mudanyali, S. Dimitrov, U. Sikora, S. Padmanabhan, I. Navruz and A. Ozcan, Lab Chip, 2012, 12, 2678-2686.
http://holomic.com/content/2012/07/01/holomic-introduces-a-smartphone-based-rapid-test-reader-at-aacc-2012/Introduction of rapid reader.
Faulstich et al in lateral Flow Imunoassay, Edited by Raphael Wong and Harley Tse, Springer 2009.
http://www.qiagen.com/about-us/contact/oem-services/ese-instruments/esequant-lateral-flow-system.
PCT Search Report and Written Opinion dated Jan. 8, 2015 for PCT/IB2014/062567 (Corresponding PCT Case to this Patent Application).
Posthuma-Trumpie et al. "Lateral flow (immuno)assay: its strengths, weaknesses, opportunities and threats. A literature survey" Anal. Bioanal. Chem. (2009) 393-569-582.

* cited by examiner

UNIVERSAL RAPID DIAGNOSTIC TEST READER WITH TRANS-VISUAL SENSITIVITY

This United States Utility Application claims priority to U.S. Provisional Application Ser. No. 61/889,821 entitled "Universal Rapid Test Reader for Lateral Flow Immunoassays with High Sensitivity", U.S. Provisional Application Ser. No. 61/845,742 entitled "Flash-controlled, Wireless, Lensless, Universal Rapid Diagnostics Test (RDT) Reader", U.S. Provisional Application Ser. No. 61/899,116 entitled "Non-uniform Flash Illumination Based focusing Method for the Imaging of Targets that are uniformly illuminated", which are commonly-owned and incorporated herein by reference in their entirety.

FIELD OF THE SUBJECT MATTER

The current application is related to a universal rapid diagnostic test reader with trans-visual sensitivity.

BACKGROUND

Rapid diagnostic tests (RDTs) play an important and growing role in the continuum of care worldwide. Administered either at the point of care in doctors offices, hospitals, urban and remote clinics, or by ambulatory health workers and providing immediate results these tests contribute to improved access, lower cost, and better quality healthcare. An increasing number of RDTs are available for home use by patients and the general public for testing of acute and chronic conditions. The dominant technology used for RDTs is Lateral Flow Immuno-Chromatographic assay (LFI) and with the worldwide annual value of LFI tests and services of $18 B according to BCC Research. RDTs are also available in other variations of immunoassays, such as fluorescent LFIs, flow-through, and dipstick tests. In fact, contemplated embodiments described here are applicable to any RDT using a change of the optical properties as the mechanism of action.

As valuable as RDTs are, they can be less reliable and accurate, because they are typically read visually, and therefore, are subject to human error [1-19]. These inherent errors can be substantially alleviated through the use of electronic readers originally developed by ESE GmBH and today available from a number of sources [21, 22]. They are typically desktop instruments for laboratory use, can be rather large and heavy and can cost thousands of dollars. Recently, significant progress in the state-of-the-art technology was achieved by Professor Aydogan Ozcan and his research group at UCLA using a smartphone as the technology platform. In addition, they developed a reader [17, 2] (hereafter Mudanyali reader) with the following advantages: a) small, handheld and light (~2.3 oz), b) sensitive and accurate with transmission or reflection readout mode, c) impervious to ambient lighting conditions, d) automated test readout with electronic data capture and telemetry using smartphone communication capabilities, e) centralized data collection with geomapping capabilities and interfaces to health information systems, and f) low cost achieved by piggybacking on the enormous production volume of smartphones.

Despite the advantages, there are opportunities available for these conventional readers to be improved. For instance, conventional systems achieve low cost by using a smartphone which is inserted into a reader body that provides RDT illumination, ambient isolation, and cassette housing. However, different models of smartphones from a single manufacturer or even more from a variety of vendors all have different mechanical dimensions, and they wouldn't fit into a body designed for one specific smartphone model. This precludes users from using their own smartphone for the reader: they have to buy another dedicated smartphone which is a significant cost increase.

Readers require sources of illumination and associated control electronics and battery housed outside the smartphone. In Mudanyali's conventional reader, the control is provided by the software application in the smartphone via a cable which plugs into the smartphone micro USB power connector. External cabling adds to the cost and reduces reliability; besides, many smartphones do not have the capability for outbound control through their power connector. Also, Mudanyali's reader describes a power source disposed in the attachment such that the self-powered reader can be controlled via a physical button located on the attachment. This operation fully depends on operator's ability to use the reader and increases the complexity of operation. It would be ideal if contemplated readers and systems corrected many of the before mentioned deficiencies of the prior art.

Moreover, Mudanyali's reader is capable of accommodating different tests types using special customized-trays per cassette type. Therefore, it doesn't provide a universal solution to image any test without additional mechanical components. A universal reader should be readily able to work with a significant number of different test cassettes without a need for any mechanical adaptation or additional mechanical components.

Recently another implementation of a smartphone-based reader has been disclosed [23], which depends on the optimized Rayleigh/Mie scatter detection by taking into consideration the optical nitrocellulose membrane and gold nanoparticles on rapid tests. For each test type, this approach requires a complicated and precise calibration procedure to determine the optimum angles of illumination that minimize the Mie scattering from the membrane while maximizing the Rayleigh scatter detection from the gold nanoparticles on and inside the membrane. Due to the significant variation between different RDT types and also the variation within the samples of same RDT type in terms of use of components (e.g., membranes and nanoparticles) and position/orientation of membrane and cassettes, successful implementation of this concept on a portable unit is quite challenging and not feasible. For instance, the coefficient of variation (CV) exceeds 50% in some of their measurements on quantitative tests [2]. This reader variation is generally not acceptable even in qualitative measurements. This alignment-dependent approach may be useful for research purposes on the analysis of custom-made immunoassays using advanced optical imaging setups that includes a precise automated scanning stage and other opto-mechanical components.

Note that although the work here was focused on smartphone-based RDT readers as the most advantageous architecture many of the technologies described herein apply equally well to any reader architecture based on digital imaging.

SUMMARY OF THE SUBJECT MATTER

A universal rapid diagnostics test reader is disclosed and described herein that includes a set of control electronics, a digital camera component, an illumination component, a housing component, and a rapid diagnostics test tray, wherein the tray can hold at least one rapid diagnostics test having a shape and a size in a fixed position relative to the digital camera component and the illumination component, and wherein the reader can accommodate more than one different rapid diagnostics test.

Methods are also disclosed that include: providing at least one first rapid diagnostics test having a first physical size, first feature and first format; providing at least one second rapid diagnostics test having a second physical size, second feature and second format; inserting the first rapid diagnostics test in a universal rapid diagnostics test reader; analyzing the first rapid diagnostics test using the universal rapid diagnostics test reader; removing the first rapid diagnostics test from the reader; inserting the second rapid diagnostics test in a universal rapid diagnostics test reader without any mechanical adjustments of the reader or without the use of any additional parts or additional inserts; and analyzing the second rapid diagnostics test using the universal rapid diagnostics test reader.

DETAILED DESCRIPTION

A universal rapid diagnostics test reader is disclosed and described herein that includes a set of control electronics, a digital camera component, an illumination component, a housing component, and a rapid diagnostics test tray component, wherein the tray can hold at least one rapid diagnostics test having a shape and a size in a fixed position relative to the digital camera component and the illumination component, and wherein the reader can accommodate more than one different rapid diagnostics test.

Many of the deficiencies as outlined earlier are corrected by the contemplated to embodiments disclosed herein. Specifically, contemplated embodiments overcome the following limitations:

Different cassette designs and mechanical dimensions make it challenging to interface with the imaging system of the reader. Contemplated embodiments work with a wide range of cassette sizes, and they avoid the pitfalls of mechanical adapters for each test type.

Conventional readers require sources of illumination and associated control electronics and battery housed outside the smartphone. In Mudanyali's conventional reader, the control is provided by the software application in the smartphone via a cable which plugs into the smartphone micro USB power connector or a physical switch that is outside the attachment. External cabling and physical switches add to the cost and reduce reliability; besides, many smartphones do not have the capability for outbound control through their power connector. Current contemplated embodiments solve this problem with a wireless control (no wires, cables or physical switches needed).

Conventional systems achieve low cost by using a smartphone which is inserted into a reader body that provides RDT illumination, ambient isolation, and cassette housing. However, different models of smartphones from a single manufacturer or even more from a variety of vendors all have different mechanical dimensions, and they wouldn't fit into a body designed for one specific smartphone model, which precludes users from using their own smartphone for the reader: they have to buy another dedicated smartphone which is a significant cost increase. Current embodiments provide a low cost way to eliminate this problem and enable the use of a wide variety of mobile devices including smartphones and tablet PCs.

Architecture

Figure 1A:
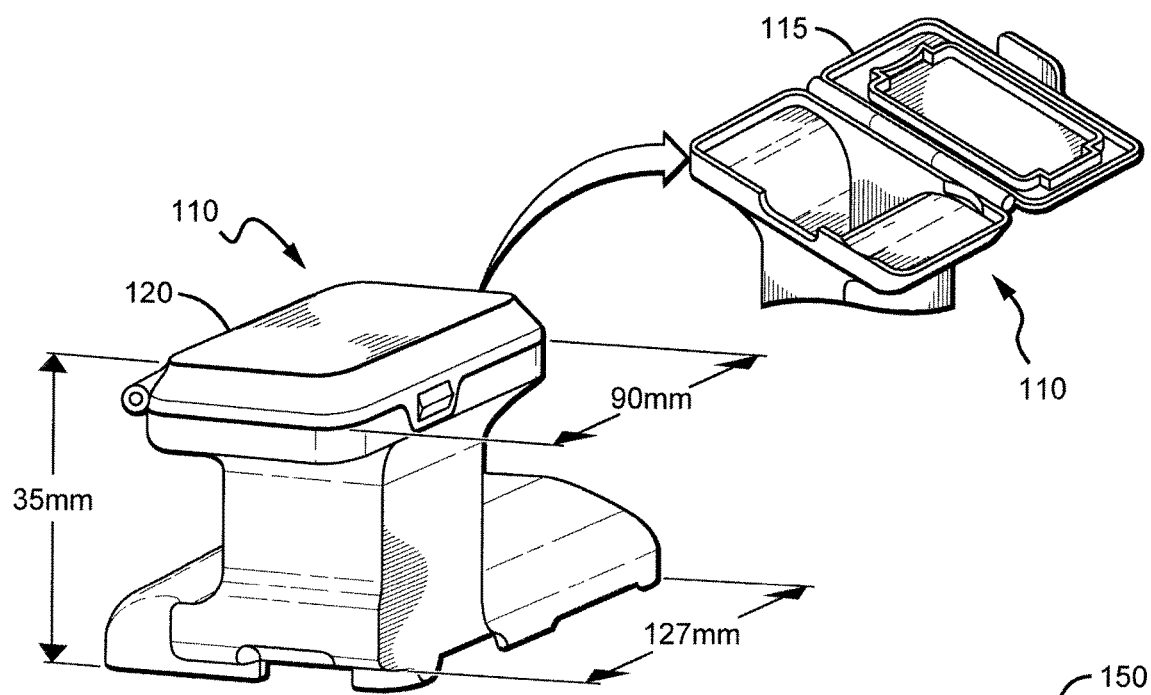
FIG. 1 shows (a) Universal RDT reader attachment that can repeatedly attached/detached to a cell-phone (b) PCB is enclosed within the reader attachment.
Figure 1B:
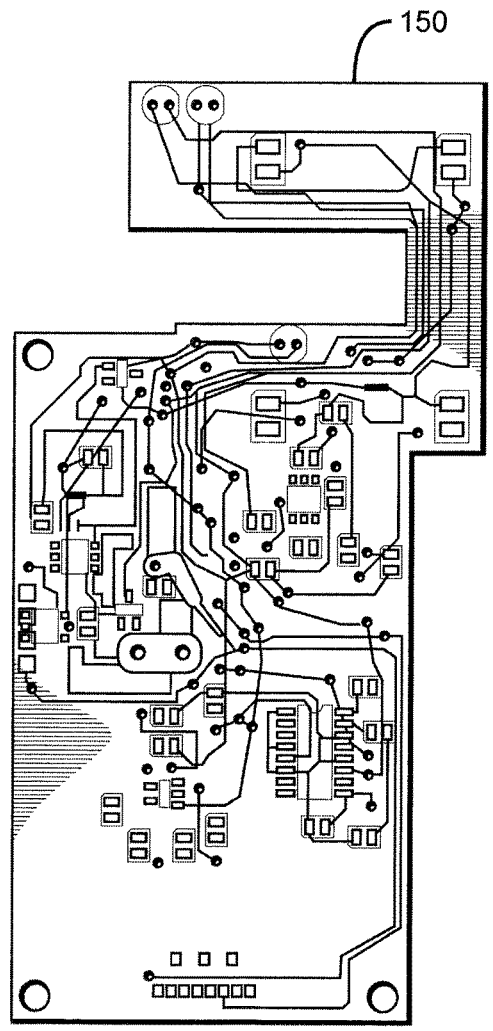

A Universal Rapid Diagnostics Test (RDT) Reader has been developed, is disclosed herein and is shown in FIG. 1A, that can accommodate multiple (at least 5 different test types with dimensions up to 35 mm×85 mm) RDTs without any need for mechanical modification or external RDT trays. FIG. 1A shows a contemplated universal RDT reader attachment 110 in an open 115 and closed 120 position. A contemplated communications device, such as a cell phone, is not shown in this Figure. In this single-piece adapter design, a printed circuit board (PCB) 150, as shown in FIG. 1B is utilized that includes multiple illumination light emitting diodes (LEDs), a replaceable and rechargeable battery, a recharging circuit with its USB port, and a photo-sensor, which is used to wirelessly trigger/control the illumination LEDs via the cell-phone application. The PCB with the battery is coupled with or affixed into the adapter. The complete reader attachment assembly is wirelessly press-fit onto a smartphone for easy mounting and demounting.

One objective of the development of contemplated embodiments disclosed herein was to introduce a rugged, wireless (controlled using cellphone flash via the photosensor), lensless (no external lens needed), smartphone based universal RDT reader that can continuously operate over extended hours even in field settings. It should be understood that the platform is cell-phone independent, such that it can be adapted to any cell-phone device with minor or no mechanical modifications. In this embodiment, we used an inexpensive and rugged Motorola Defy XT 535 smartphone. It includes optical and electrical components embedded on a printed circuit board (PCB) that is powered by a rechargeable battery, which can operate over 12 hours without any need for external power. This contemplated universal reader, without any modification on its mechanical architecture, accommodates and digitally interprets a broad range of RDTs to diagnose chemical and biological threats and other diseases.

The sensitivity and accuracy of the platform was demonstrated by conducting repeated measurements on positive (including the ones activated by highly diluted positive control samples) and negative tests. Through a custom-developed smartphone application, the integrated smartphone-based reader labels digitally processed test results with spatiotemporal information and transfers them to central data collection points (servers) that can be accessed locally and globally.

Figure 2A:
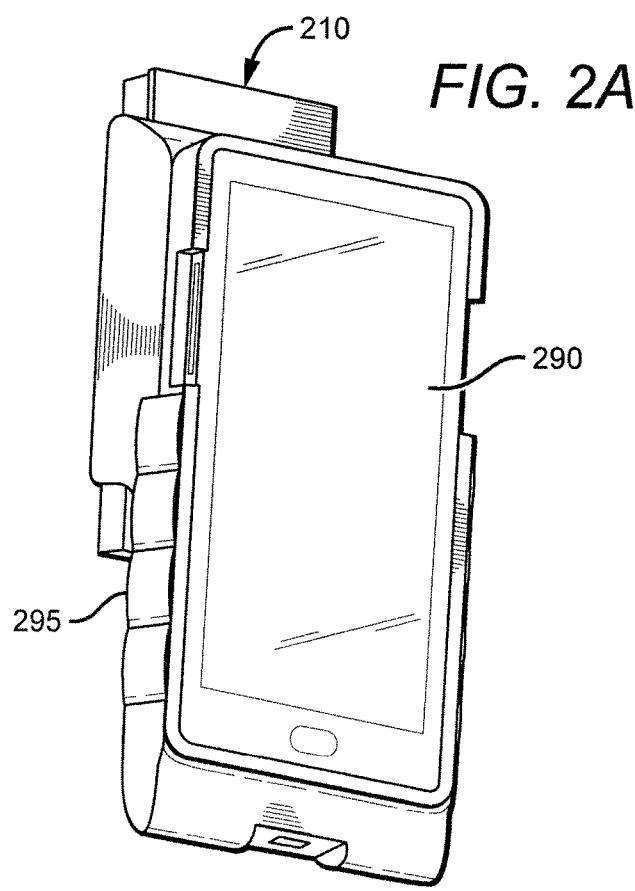
FIG. 2 shows (a-b) Different schematic views of proposed universal RDT reader prototype installed on an Android phone (Motorola Defy XT 535). This compact attachment can be repeatedly attached/detached to the smartphone body without the need for fine alignment and any modification. (c) Mechanical body of the reader attachment will also ensure the isolation to the RDTs that are loaded to the smartphone reader attachment using a universal test tray. With its slip-free grip design, it allows the user to conveniently hold it even in the field settings. It includes a single USB port with a photo-sensor to communicate with both smartphone and the PCB board. Having an unconventionally large field-of-view of ~45 mm×85 mm, this attachment will also allow the user to acquire images of other objects of interest, such as user ID card (e.g., military) and RDT pouch with type/lot numbers, while the universal RDT tray is retracted from the base attachment assembly. (d) Reader attachment uses inexpensive optical components, i.e., a plano-convex lens (optional) and multiple diffused narrow-band LEDs embedded on a single PCB that also carries circuitry for the data and power communication with the smartphone and rechargeable flat or AA batteries, respectively. (e) Schematic diagram of the proposed optical geometry is shown. (f) Flexible lens assembly is demonstrated. Utilizing an external diffuser and a narrow band-pass (<30 nm) filter, flash light of the smartphone can be used to potentially support or mimic the LED illumination. Without any modification on the architecture of the main mechanical body (c), lens holder can be modified to hold the additional diffuser and band-pass filter as shown in (f).
Figure 2B:
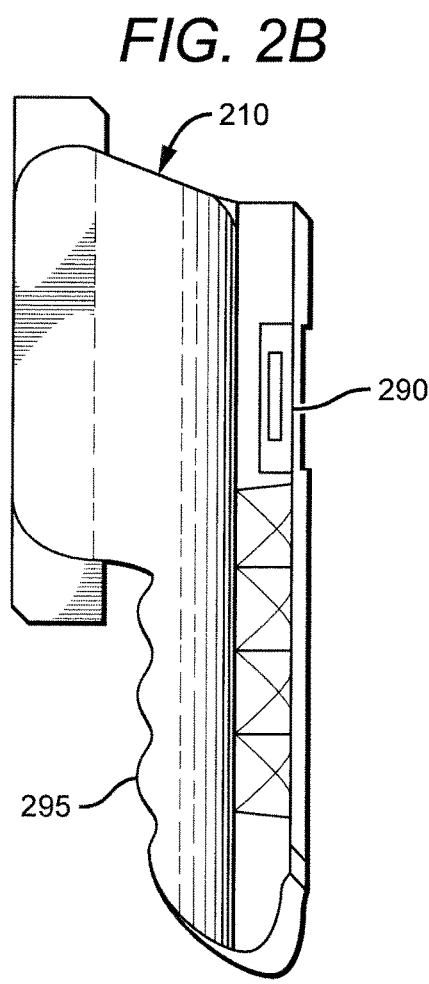

This smartphone-based RDT reader and spatiotemporal threat/disease monitoring platform utilizes a compact snap-on smartphone attachment 210 that can be repeatedly attached/detached at the back 295 of the smartphone devices 290 (see FIGS. 2A and 2B) to acquire digital images of RDTs. This scalable attachment is designed to fit different smartphone devices (e.g., iPhone or Android phones and tablets) and can be simply adapted with minimal or no engineering.

Figure 2C:
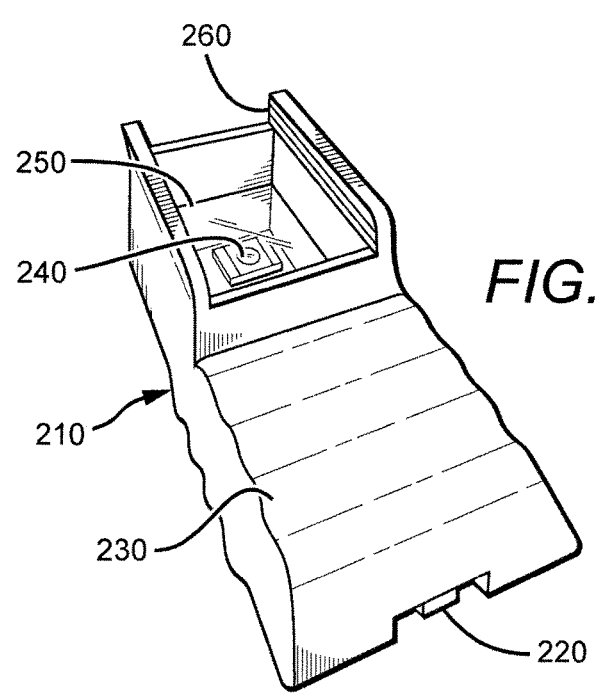

The mechanical body of this independent reader attachment is designed to be robust and easy-to-handle by the user and initially prototyped using a 3-D printer, which uses ABSplus™ modeling material, a recyclable and eco-friendly thermoplastic. For volume manufacturing using different techniques (e.g., injection molding or casting), other material types with different material properties can be used. This snap-on reader attachment utilizes inexpensive optical components and printed circuit boards with various electrical components i.e., multiple LEDs (light emitting diodes) and/or LED arrays, a photo-sensor interface to wirelessly control and trigger the illumination LEDs (via the cell-phone application), rechargeable battery as well as a recharging circuitry and its USB port embedded on the same. (see FIGS. 2C and 2D). In FIG. 2C, a contemplated device 210 is shown with a USB connector 220, a "slip-free" grip design 230, a lens assembly 240, protection glass 250 and an "error proof" multi-track system 260. In FIG. 2O, the back of a contemplated device 210 is shown with the USB port or connector 220, a recharging circuit 221, a battery holder 222, a LED driver circuit 223, an audio port 224 and at least one LED bar 225. Please note that this reader attachment does not require the use of any external lenses for the magnification/demagnification of the RDT image, however it has an optional tray that allows the user to utilize an additional imaging lens (optional) to meet to requirements of different imaging conditions.

Another important design consideration is the choice of ROT illumination scheme that has a significant effect on the sensitivity and accuracy of the test interpretation. Embedded on a single PC board, multiple diffused LEDs can be used to illuminate (with an illumination angle close to normal incidence) the RDT under test (see FIG. 2D) in both reflection and transmission modes (butt-coupled to the ROT under test). The PC board can also a high-power UV led for the digital evaluation of fluorescent tests. Unlike reflection and transmission mode LEDs, UV led is positioned with angle of ~30-50 degrees to excite the tests of interest. Powered by an embedded rechargeable battery, LEDs are wirelessly controlled by a photo-sensor mounted on the PCB. The smartphone application, based on the user's selection, digitally configures and utilizes the flash of the cell-phone to trigger the photo-sensor and control the illumination LEDs automatically during testing. This wireless and digital communication with the illumination LEDs allows the software application to turn on the LED arrays only during image acquisition and observation, decreasing the power consumption for extended battery life.

Figure 2D:
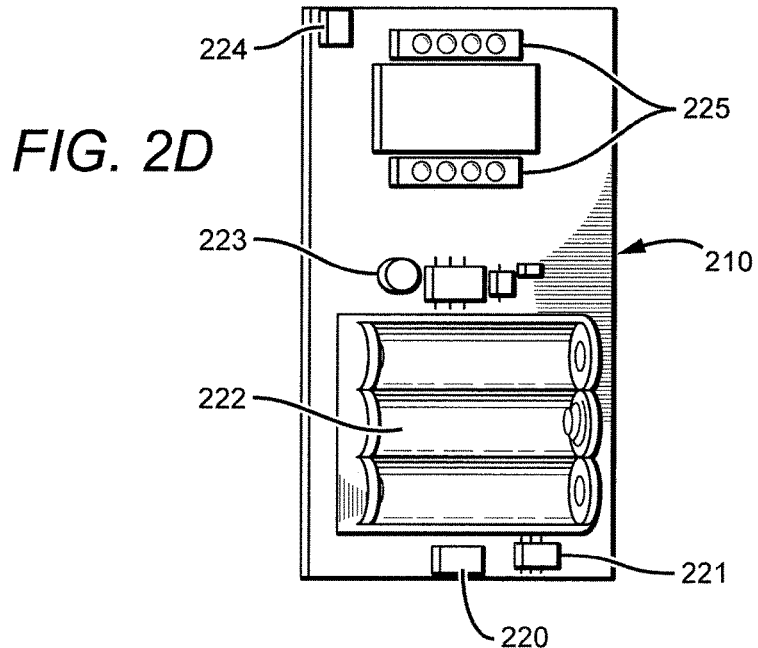

Furthermore, as shown in FIG. 2D, the PCB board also has a custom-designed circuitry with an integrated USB port or connector to recharge the battery of the reader attachment without any need for additional equipment, simply by sharing the smartphone USB cable within the base mechanical body. Moreover, by using this external battery, a contemplated ROT reader is able to evaluate >1000 RDTs and operate longer than 12 hours without any need for external battery and recharging. Applying <10 second exposure for image acquisition per test, this enables rapid readout of stacked RDTs without an interruption.

Rather than using broad-band light sources (e.g. ambient light) with varying intensity profiles and optical spectrum, the use of special LED illumination can significantly increase the contrast between the control/test lines and the background on RDT images, provided that the wavelength of the illumination is optimized based on spectral measurements. For instance, test pads (e.g., nitrocellulose membrane) of most commercially-available RDTs produce distinct color signal by the immobilization of colloidal gold-labeled antigen (e.g., analyte) and antibody (e.g., binding proteins) complexes, exhibiting similar spectral properties. Based on our initial tests on various RDTs in the market, the use of LEDs with a peak wavelength of between 520 and 590 nm provides the highest contrast if colloidal gold nano-particles are used to label target antigen or antibody (in both reflection and transmission modes). It should be noted that this optimum center wavelength was determined based on spectral measurements on colloidal gold-based RDTs that are widely commercially available. Together with the custom-developed image processing algorithm that is discussed later, optimization of the illumination wavelength has primary importance on the trans-visual sensitivity of this smartphone based reader platform.

Figure 2E:
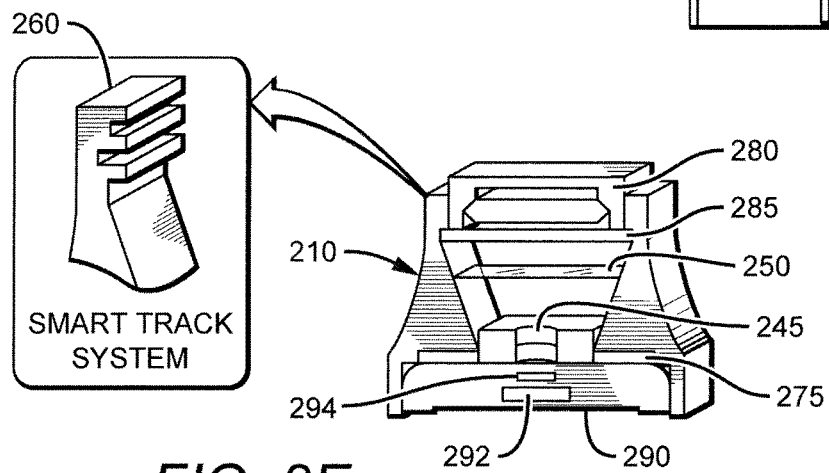
Figure 2F:
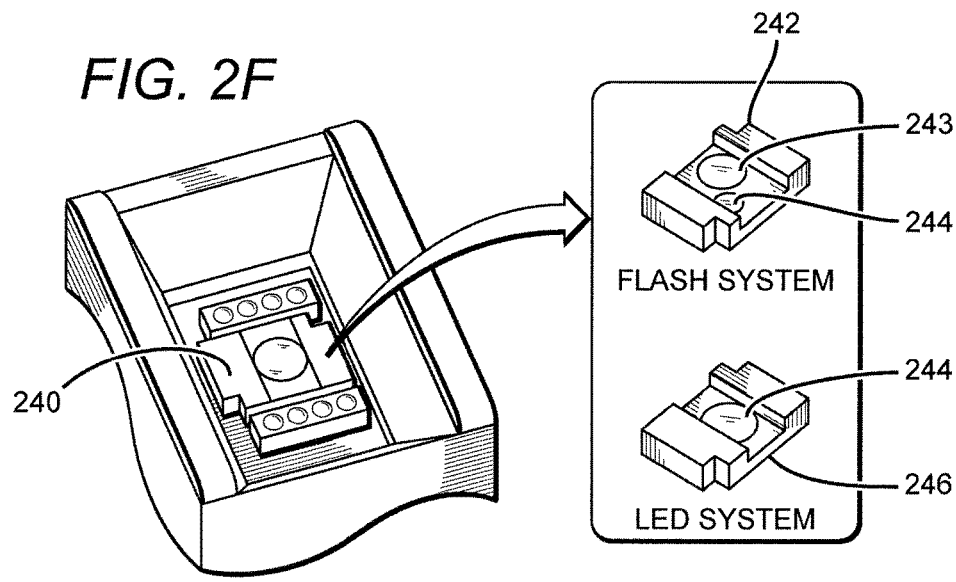
Figure 3A:
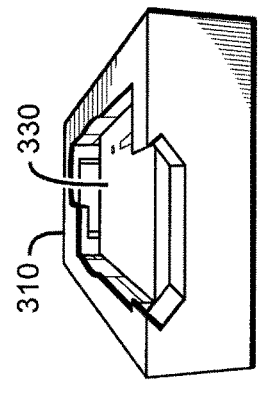
FIG. 3 shows one of the major objectives of this development was to enable universal operation using the RDT reader, such that it can accommodate a broad range of RDTs without a need for using multiple customized RDT trays and any modification on the reader attachment. Here we propose a single universal RDT tray (b) that will accommodate multiple (at least seven) RDT types. Starting with a selection of seven RDTs we conceptually designed the universal tray that allows the user to press-fit the RDTs based on a variety of orientations and heights. Following the identifiers printed on this universal tray, user can easily decide on the direction and orientation of the particular RDT to be inserted and load the universal tray into the base reader attachment as shown in FIG. 1(a-c). This design feature overcomes the need of using individual trays and attachment customized for each RDT, having an important advantage especially in the field settings. It will also provide significant reduction on material cost. In (a), different views of the universal tray loaded with different RDTs that will tested within the proposal timeline are shown. RDTs that will be examined using the proposed RDT reader in this proposal: (1) Oratect Plus (Branan Medical Corp.) for drug screening, (2) ThyroChek (Thyrometrix, Inc.) for Thyrotropin screening, (3) BioThreat Alert™ Test (Tetracore, Inc.) for anthrax diagnostics, (4) Cardiac Panel Test (MP Biomedicals, LLC) to screen cardiac markers, (5) OptiMAL-IT Malaria RDT (Bio-Rad), (6) Uni-Gold™ HIV RDT (Trinity Biotech), (7) a custom hand held assay for bacterial antigen detection (developed by ECBC).
Figure 3A:
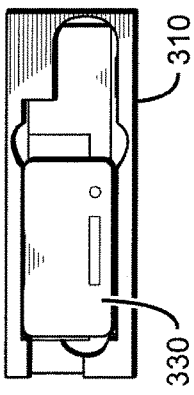
Figure 3B:
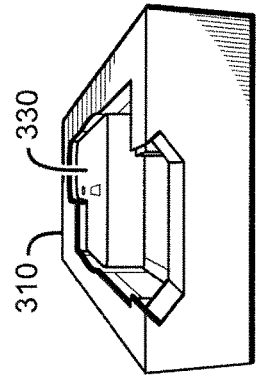
Figure 3B:
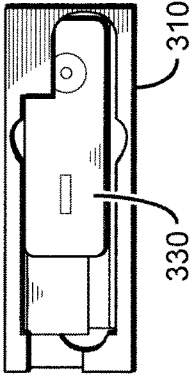
Figure 3C:
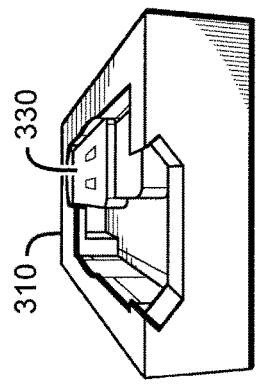
Figure 3C:
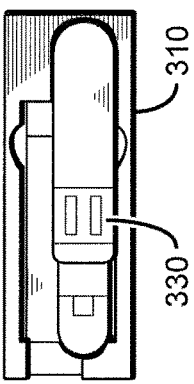
Figure 3D:
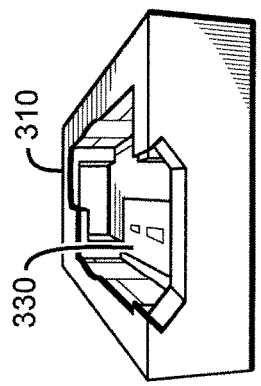
Figure 3D:
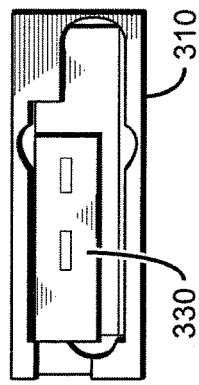
Figure 3E:
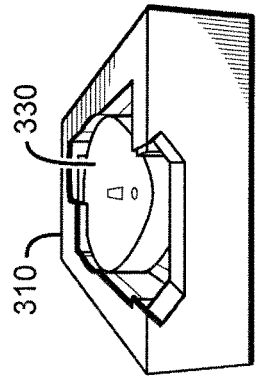
Figure 3F:
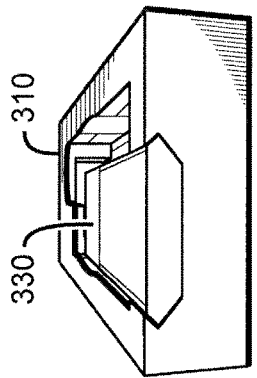
Figure 3F:
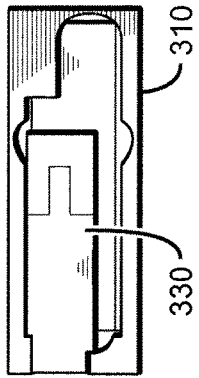
Figure 3G:
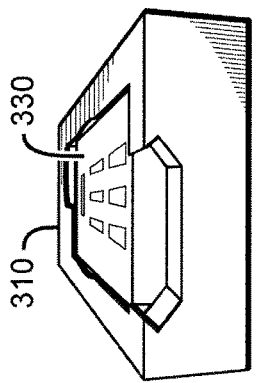

In parallel to the proposed LED illumination scheme, the use of the flash light was examined as an additional illumination source that is already available in the camera smartphone devices (see FIG. 2F). FIG. 2F shows a lens assembly 240 wherein two different systems are disclosed: a flash system 242 having a diffuser 243 and a lens 244 or a LED system 246 having a lens 244, whereby one of these systems is installed in the lens assembly 240. Locating a band-pass filter (optional) that is butt-coupled to the flash light, flash can be alternative to the LED illumination that has been described above (in both reflection and transmission modes). Although the use of external LEDs has significant advantages, such as high power output, optical design flexibility and illumination uniformity, implementing the camera flash light on the RDT reader, as an option for less demanding applications, can eliminate the need for using LEDs, electrical components, and external battery. In reflection mode, by simply locating a band-pass filter (e.g., with 520-590 nm pass-band), the flash light can replace the reflection mode LEDs. On the other hand, flash light can be also used for the transmission mode imaging. A reflection element such as a mirror can be placed at the top wall of the attachment to reflect the image of the RDT that is positioned in front of the flash for transmission mode imaging. Reflected image of the RDT can be then imaged by the cell phone camera (see FIG. 14).

Cassette Tray

Enclosing the optical imaging interface, the mechanical body of the reader attachment will also ensure the isolation to the RDTs that are loaded to the smartphone reader attachment as shown in FIGS. 1 and 3. Prior to digital evaluation, an RDT is press-fit into a unique cradle on the tray in an easy, reliable, and error-proof operation. On the interior side of the universal tray, a series of cradles are formed by ridges at different heights, orientations and lateral extensions, as shown in detail in FIG. 3, for 7 different RDTs. A computer-aided optimization and design methodology used to design this universal tray is akin to solving a three-dimensional puzzle and can be readily applied to a different set of RDT shapes and sizes.

Without any modification on the base reader attachment shown in FIG. 2E, multiple trays can be used that are capable of holding at least 5 kinds of RDTs each. FIG. 2E shows a contemplated device 210 where a smartphone 290 is connected having a CMOS or complementary metal-oxide semiconductor 292 and a lens 294. An additional lens 245 is shown, with the protective glass 250 and the smart track or multi-track system 260. The PCB 275 is also shown. A RDT tray 280 and the tray lid 285 is also shown. As a matter of fact, this innovative design eliminates the need of using an individual customized tray for each RDT type and significantly decreases the material cost and logistical problems, enabling ease-of-use even in the field settings. By the optimization of this innovative approach, the mechanical interface (tray) can be designed to accommodate different and larger groups of RDTs. It is also important to underline that this universal tray fully encloses the RDTs of interest (see FIG. 2A-F) to tackle potential ambient light leakage into the optical attachment. Since RDT material/packaging may behave as a waveguide that couples the ambient light to the optical imaging interface, this universal tray design is a vital design feature to ensure the repeatability of the measurements.

Moreover, the proposed RDT reader attachment will have a physical opening (i.e., field-of-view) of ~45 mm×85 mm to accommodate this universal tray carrying a wide range of RDTs (see FIG. 3A-G). FIGS. 3A through 3G show various RDTs 330 that are coupled with the RDT reader attachment 310, wherein the ROT reader attachment is shown in a side view (upper view) and an above perspective (lower view) in each Figure. Users can rapidly replace an already evaluated RDT with a new one to be tested without having any mechanical difficulty, thus enabling testing of large number of stacked RDTs in a short time.

Also, it also allows the user to acquire images of other objects of interest, such as user ID card and RDT pouch with type/lot numbers, while the universal RDT tray is retracted from the base attachment assembly. Digitally linked to the test results, these additional images can be processed to extract the relevant identification and security information. Note that the unconventionally wide field-of-view introduced here to accommodate a broad range of RDTs provides an opportunity to acquire images of even larger RDTs with larger dimensions or non-planar packaging (i.e. urine cup) by partially sacrificing the compactness of the reader attachment. An embodiment of these design principles is shown in FIGS. 4-6.

Figure 4:
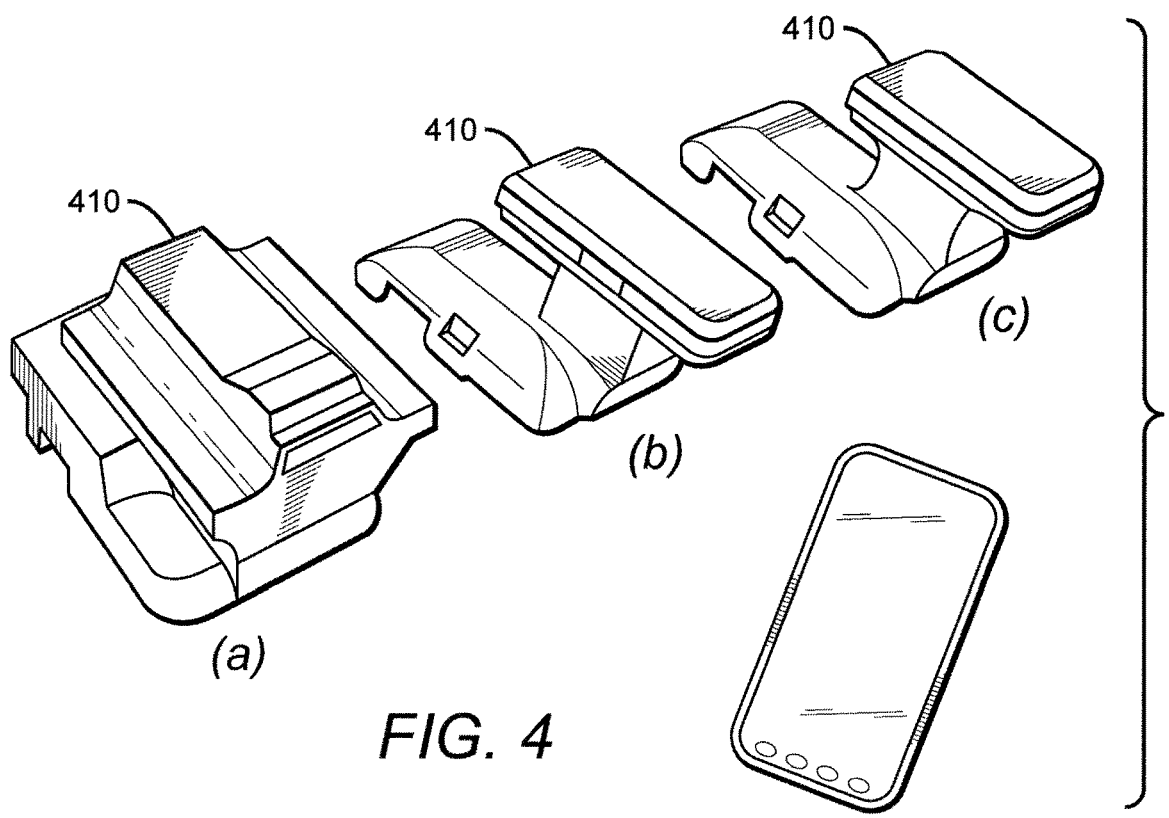
FIG. 4 shows (a, b, c) Photo of the Rapid Test Reader prototypes fabricated using a 3-D printer. (a) A prototype with a slip-on universal RDT tray can accommodate up to 7 different RDTs (b) A single-piece design that with relatively smaller dimensions can accommodate and fully enclose up to 7 different RDTs (c) A third single-piece design that can fully enclose and accommodate up to 5 different RDTs has significantly smaller dimensions and weight as well as smooth edges and corners. (d, e, f) Different types of RDTs, e.g., Uni-Gold™ HIV RDT (d), Cardiac Panel Test (e) and a custom hand held assay (f) can inserted to the prototype shown in (c). (g) and (h) Different views of the reader prototype shown in (c).

FIG. 4 shows (a, b, c) Photo of the Rapid Test Reader prototypes 410 fabricated using a 3-D printer. (a) A prototype with a slip-on universal RDT tray can accommodate up to 7 different RDTs (b) A single-piece design that with relatively smaller dimensions can accommodate and fully enclose up to 7 different RDTs (c) A third single-piece design that can fully enclose and accommodate up to 5 different RDTs has significantly smaller dimensions and weight as well as smooth edges and corners. (d, e, f) Different types of RDTs, e.g., Uni-Gold™ HIV RDT (d), Cardiac Panel Test (e) and a custom hand held assay (f) can inserted to the prototype shown in (c). (g) and (h) Different views of the reader prototype shown in (c).

Figure 5:
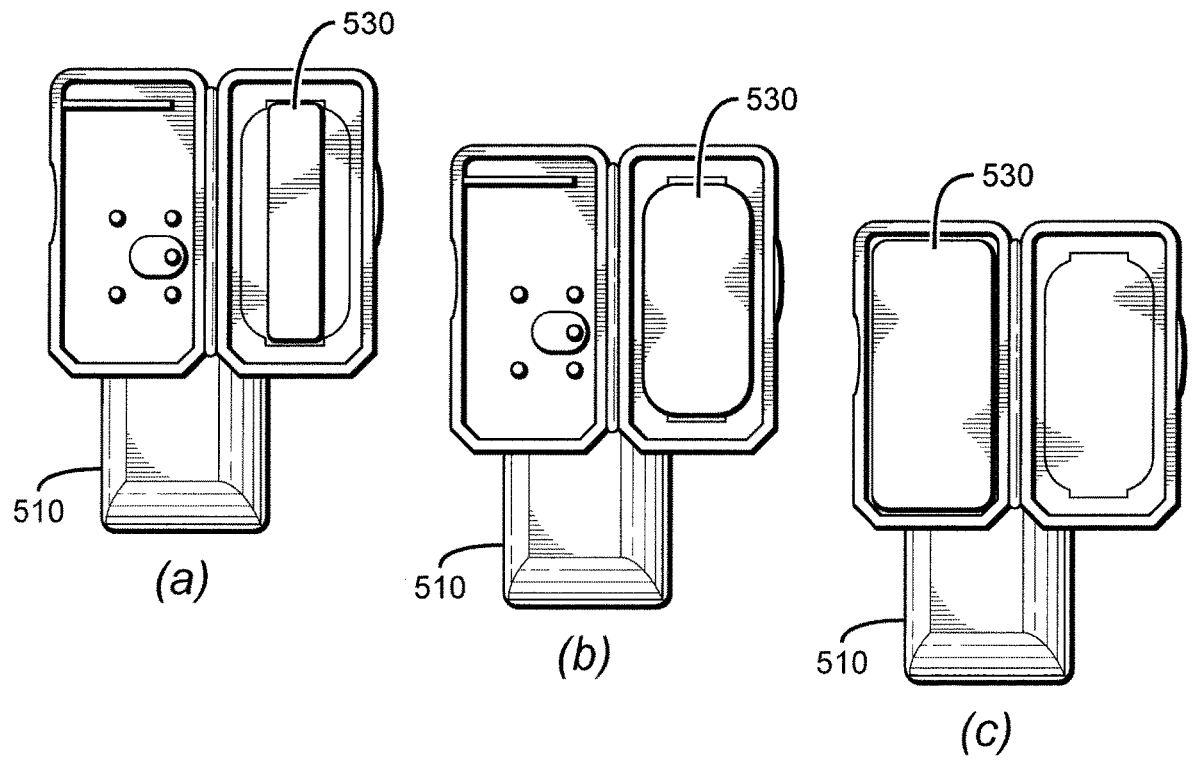
FIG. 5 shows views of the reader with its two-sided tray design for all five different ROT types, including, (a) Afla-V aflatoxin ROT (70×27×8 mm), (b) BioThreat Alert™ Anthrax ROT (62×30×6 mm), (c) Cardiac Panel ROT (80× 32×5 mm), (d) a custom hand held assay (70×20×5 mm) and (e) Uni-Gold™ HIV RDT (Trinity Biotech) (39×18×6 mm). Accommodating three out of five ROT types, the tray lid can be replaced with another one to accommodate other RDT types without any modifications on the main body of the attachment.
Figure 5:
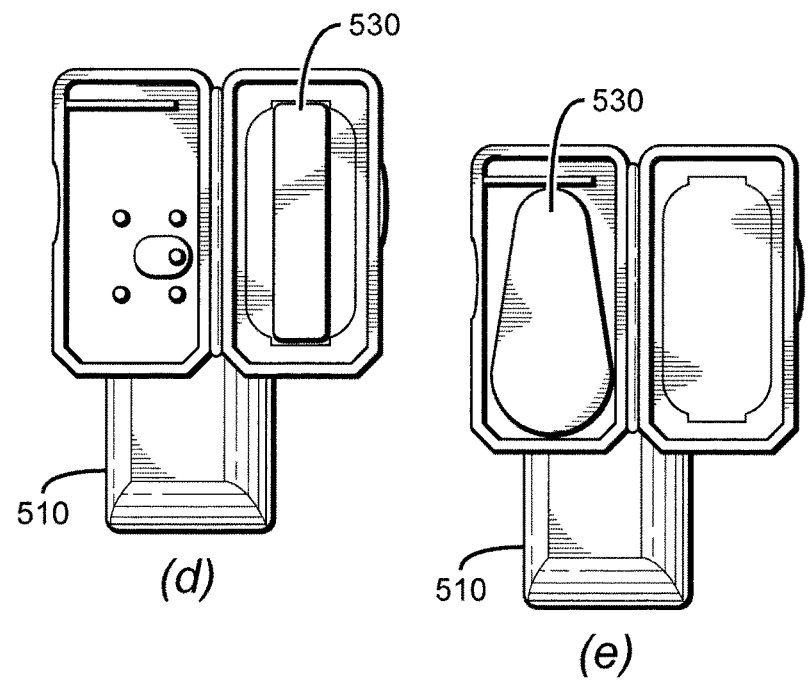

FIG. 5 shows views of the reader 510 in an open embodiment showing its two-sided tray design for all five different RDT types 530, including, (a) Afla-V aflatoxin ROT (70×27×8 mm), (b) BioThreat Alert™ Anthrax RDT (62×30×6 mm), (c) Cardiac Panel RDT (80×32×5 mm), (d) a custom hand held assay (70×20×5 mm) and (e) Uni-Gold™ HIV RDT (Trinity Biotech) (39×18×6 mm). Accommodating three out of five RDT types, the tray lid can be replaced with another one to accommodate other RDT types without any modifications on the main body of the attachment.

Figure 6:
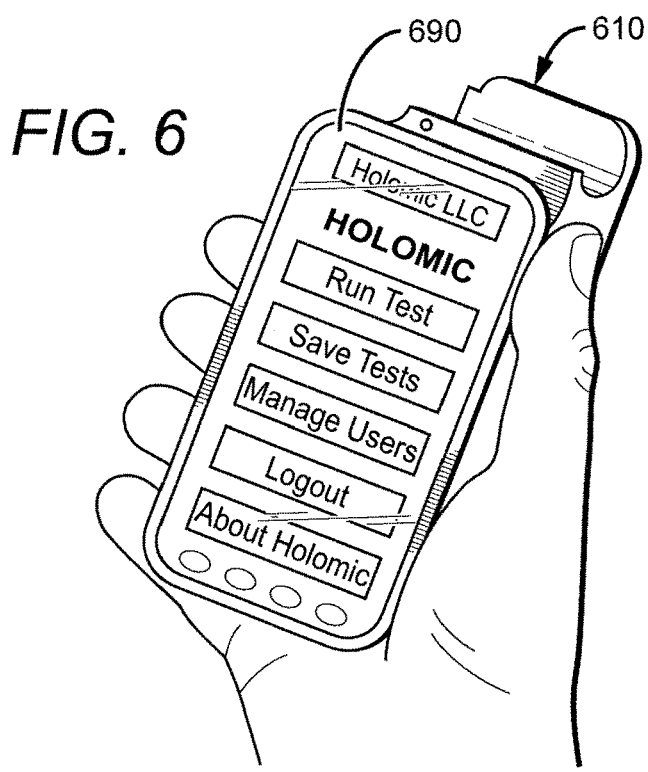
FIG. 6 shows a view of the reader functionalities.

FIG. 6 shows a view of the reader 610 with a display of the main menu of functionalities as shown on the smartphone 690 attached.

Figure 7A:
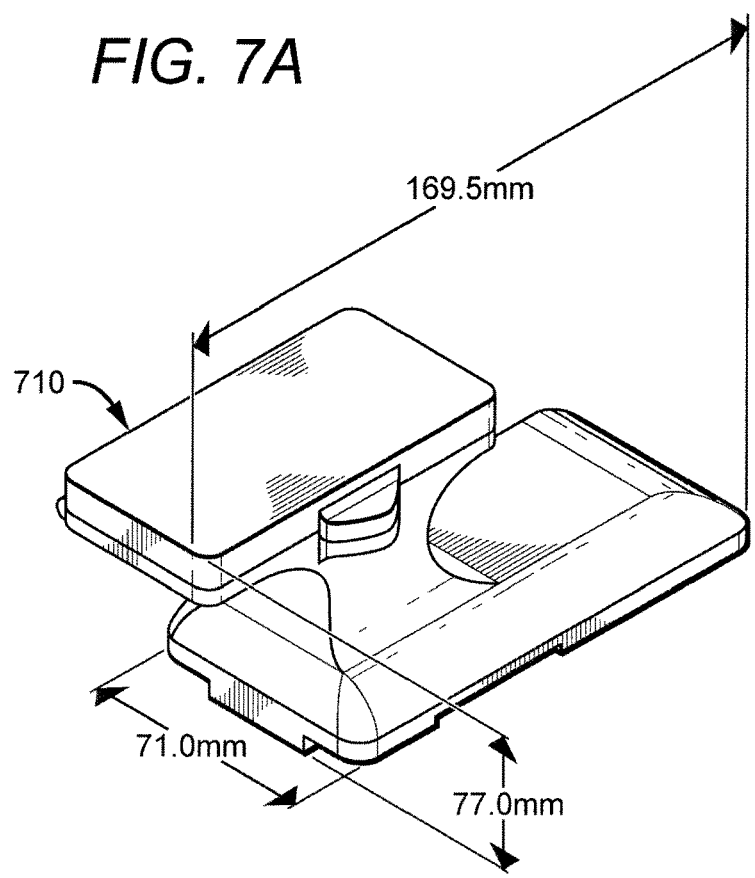
FIG. 7A shows one-design-fits-all universal cassette holder.
Figure 7A:
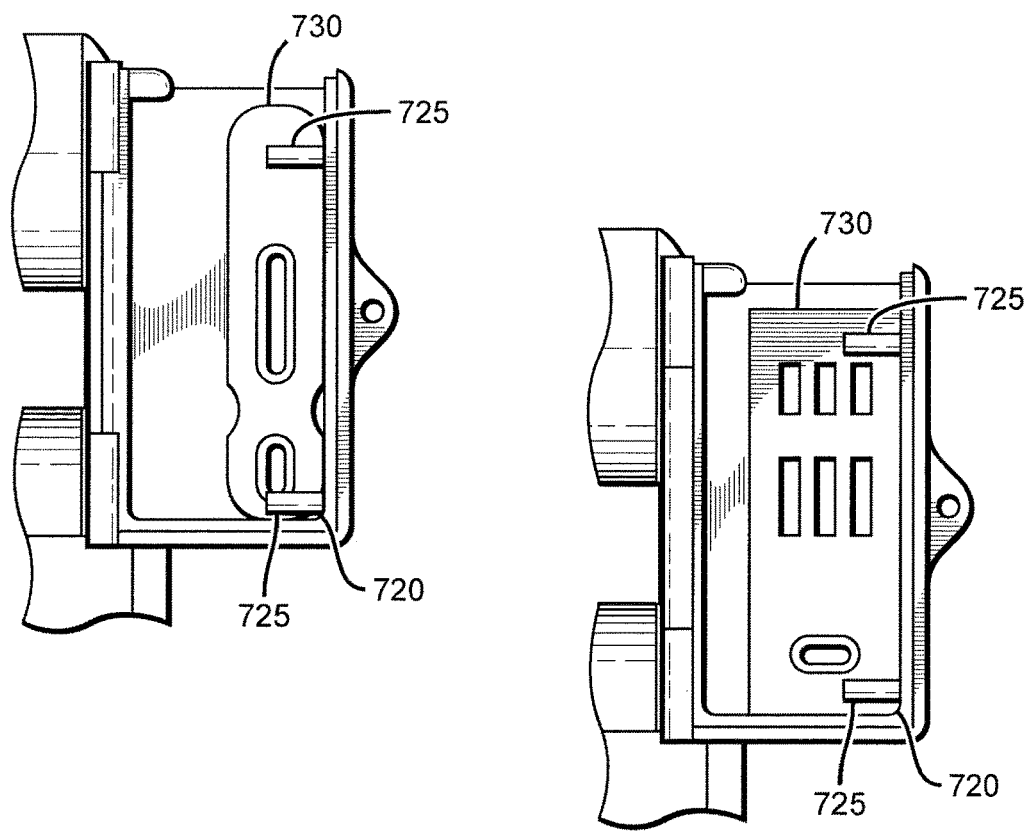

An alternative contemplated design for a universal cassette holder 710 is shown in FIG. 7A. In this contemplated embodiment, the position of the cassette 730 is fixed by pushing it against an L-shaped ridge 720; the cassette is kept in place by one or more leaf springs 725. By leaving the two sides of the cassette unconstrained, this design can accommodate a wide variety of shapes and sizes with a single design. This kind of flexibility is a huge advantage for the manufacturer and the users. Rather than just pushing the cassette into the only cradle it would fit, now the operator must make sure that the cassette fits snugly in the corner of the L. Also, for a triangular or other non-rectangular shapes the test strip is at an angle but this is easily handled by the software (application running on the cell-phone). Moreover, this flexible approach, without any hardware and software modifications, may allow the user to work with emerging next-generation technologies (flow through tests) that will be available at the markets in the near future.

Figure 7B:
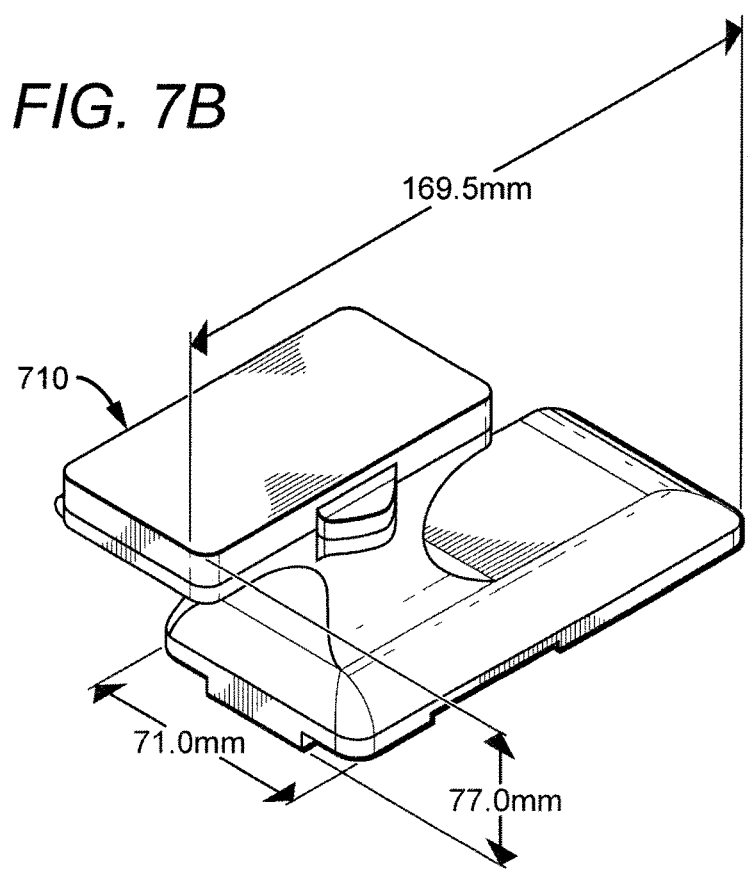
FIG. 7B shows universal Tray with a spring to accommodate any test that has dimensions of 85 mm by 35 mm or smaller.
Figure 7B:
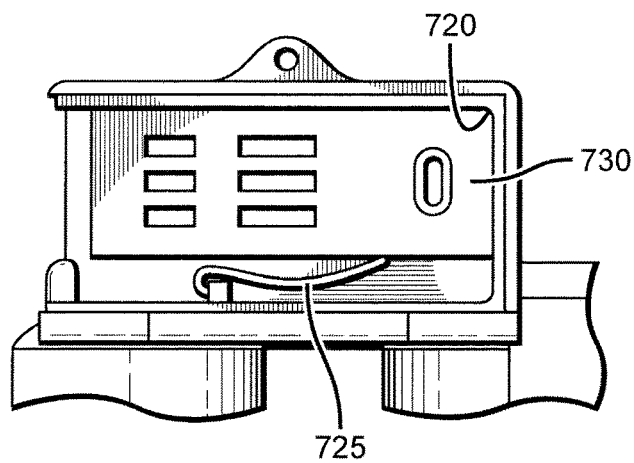
Figure 7B:
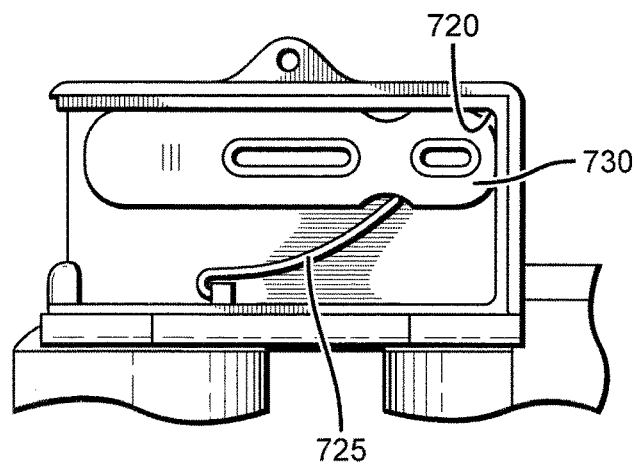
Figure 7C:
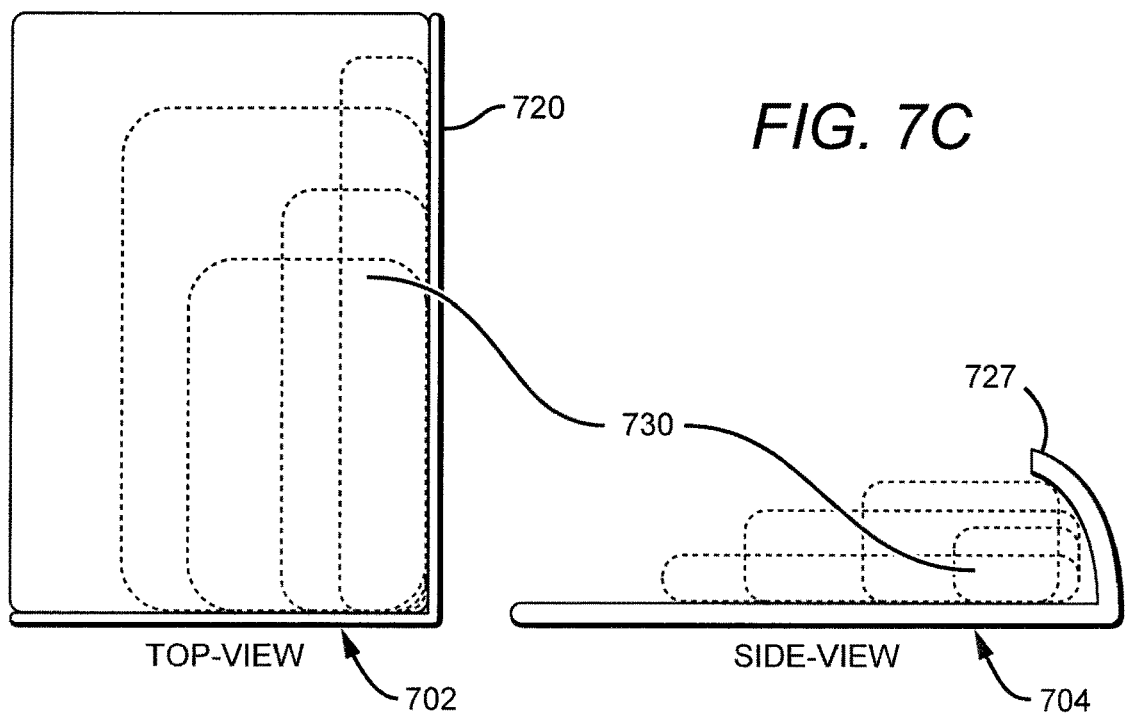
FIG. 7C shows top-view schematics of the tray (left) and side-view schematics of the tray (right).

In addition to the designs shown in FIG. 1A and FIG. 7A, a completely universal and user-friendly tray design 710 has been developed for contemplated readers (FIG. 7B). The designs are based on the concepts shown in FIG. 7C: by constraining the position of the RDT 730 in one plane only by an L-corner 720 and in the perpendicular direction by a slanted or curved side (727 in FIG. 7C) it is possible to accommodate a wide range of RDT shapes and sizes in the same tray. This design utilizes another contemplated flat tray with a spring 725 placed on the side wall to keep the cassettes, which can simply slide into the tray, in place. In this design, the tray has only three walls with an opening at the top for the user to slide in the test cassettes of interest. The position of the cassette is fixed by pushing it against to the side of the tray; the cassette is kept in place by one or more leaf springs. This design allows the user to work with any cassette type that is smaller than 85 mm by 35 mm. By simply modifying the tray (test interface, not the main body of the attachment), these dimensions can be further increased. On the other hand, operator inserts the cassettes into this mechanical interface by sliding them in all the way into the tray such that ideally the cassette should fit in the L-corner. However, unlike the drawback of the design in FIG. 7A, the potential shift due to the failure of the operator will be only in longitudinal direction—not in other directions. Our smart cell-phone application will recognize such vertical shifts on the position of test casettes and either digitally compensate for it and evaluate the test or warn the operator to correct the position of the test cassette. Alternatively, a second spring could be implemented on the fourth side of the tray to ensure positive contact with the L-corner. To keep the cassette from falling out of its position, a third spring or springs could be mounted on the top of RDT. Alternatively, at least one of the tray sidewalls could be slanted 727 or curved as shown in FIG. 7C; note that different cassette thicknesses 730 all fit in with only a slight lateral displacement. In FIG. 7C, a top-view 702 and a corresponding side-view 704 is shown.

Readout

Figure 8:
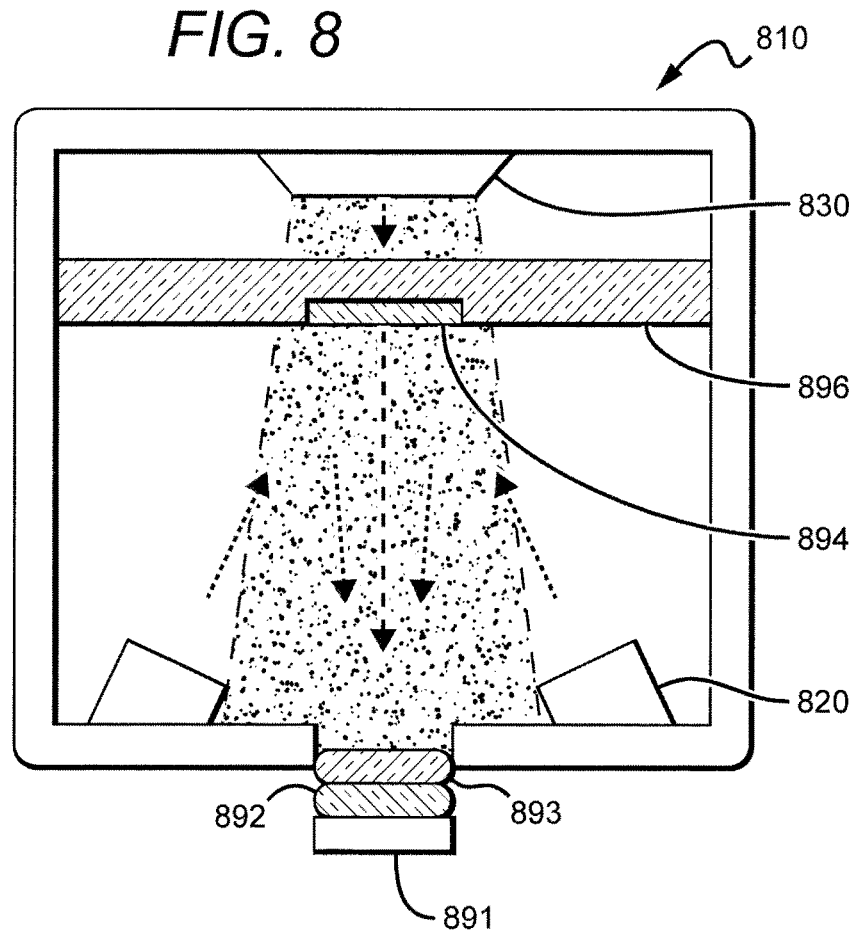
FIG. 8 shows reflection and transmission readout modes.
Figure 9:
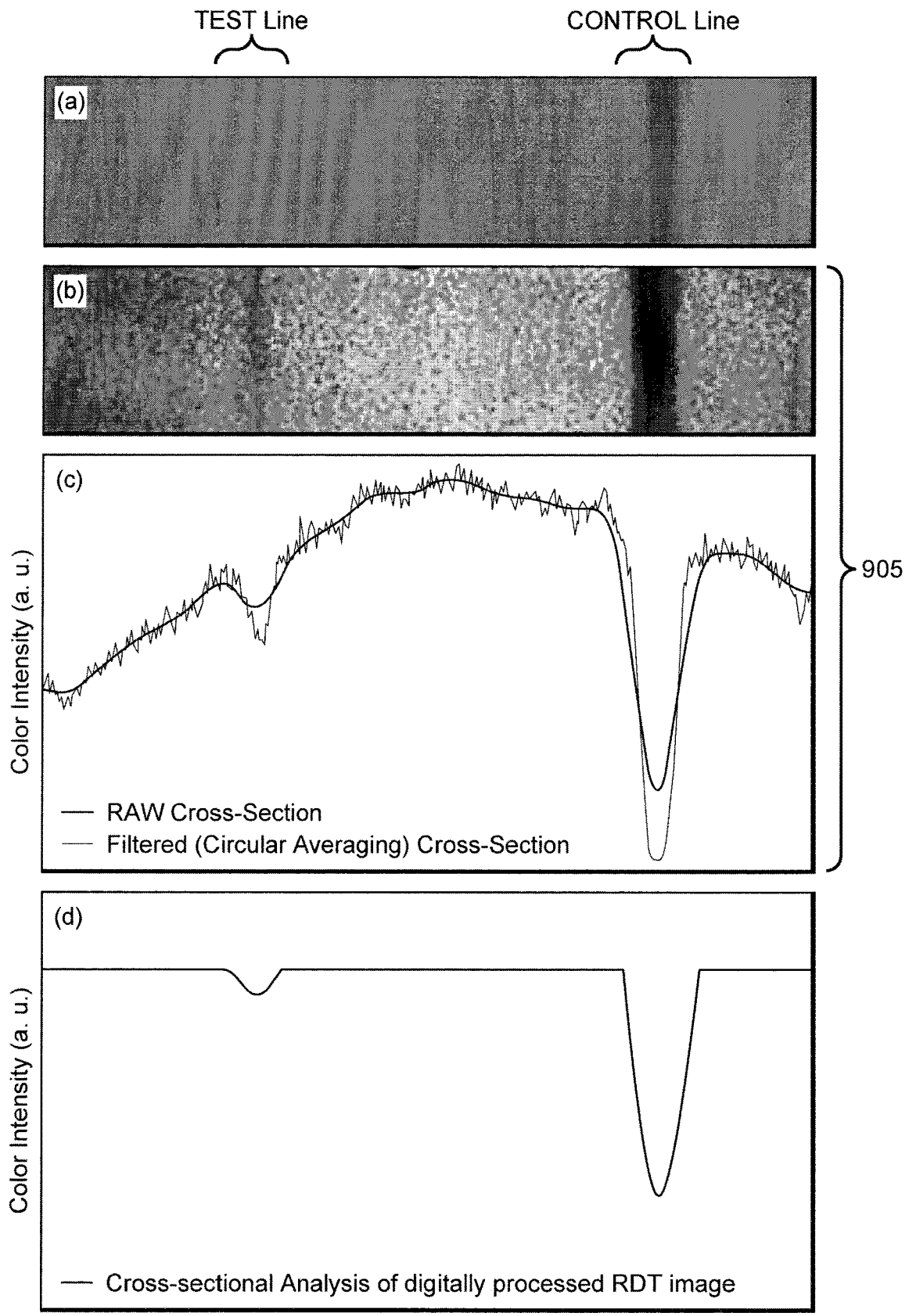
FIG. 9 describes that we have conducted initial measurements to test the performance of the proposed optical imaging scheme and digital image processing algorithm by analyzing a Bio Threat Alert™ RDT (Tetracore activated using highly diluted positive control sample. In order to simulate the proposed reader platform, we conducted this measurement with a Samsung Galaxy smartphone mounted on an optical table with adjustable optical and mounting components. For the illumination of RDT under test, two narrow-band LED arrays (wavelength=565 nm, bandwidth=~30 nm) were used. (a) Prior to acquire RDT image using the proposed optical scheme, under ambient light, we have recorded a basic smartphone camera image in the room conditions, providing no distinct color intensity (on the test line) that can be identified by human eye. However, in the digitally processed and enhanced image of the same RDT acquired using our optical platform (b), digital contrast level has been significantly improved between the test line and the background. (c) Although there has been an analyte-generated background in this RDT image, our derivative-based filter has corrected this issue, enabling the recovery of test as well as control line free from the chemical and optical background noise.
Figure 10:
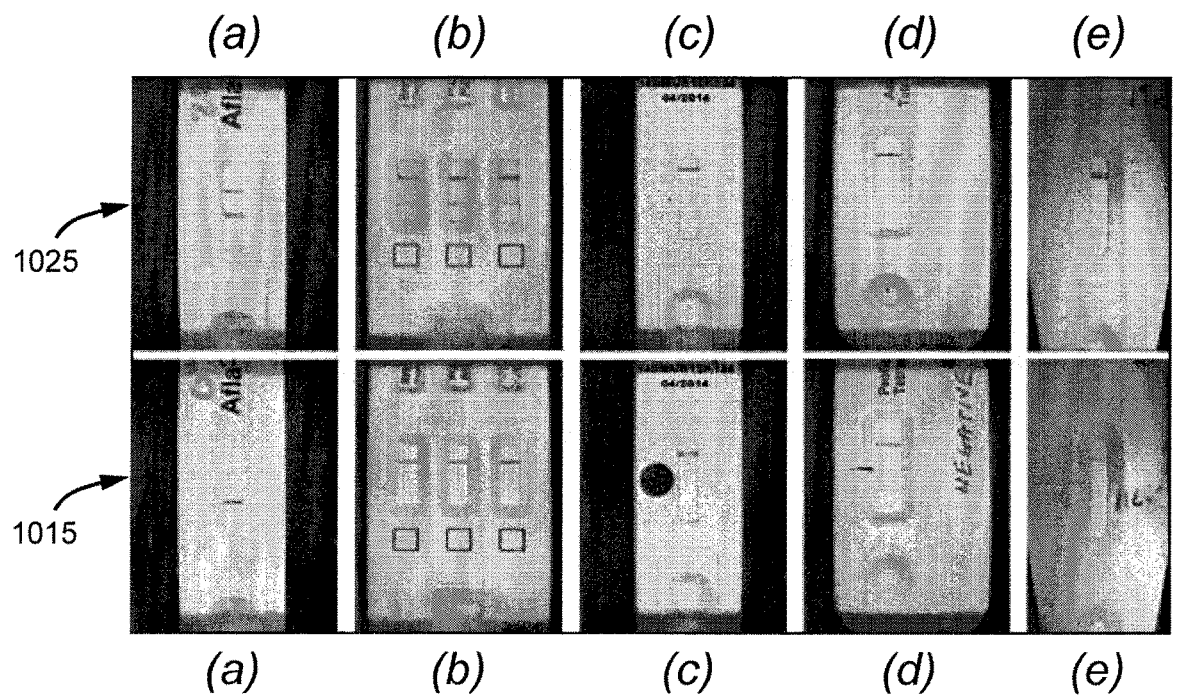
FIG. 10 shows exemplary (recorded and automatically processed) images of negative (bottom row) and positive (top row) tests for (a) Afla-V aflatoxin RDT, (b) Cardiac Panel RDT, (c) a custom hand held assay developed by ECBC (Edgewood Chemical Biological Center), (d) Bio-Threat Alert™ Anthrax ROT, and (e) Uni-Gold™ HIV ROT (Trinity Biotech).

A contemplated reader 810, like the conventional readers disclosed earlier, has three readout modes: fluorescent (not shown), reflection mode 820 and transmission mode 830, as shown in FIG. 8. The reflection mode 820 is used in all available readers as it obviously parallels visual readout, it is easy to implement, and provides comparable results. FIG. 8 shows the cell phone camera 891, the cell phone camera lens placement 892, an external imaging lens 893, an orasure test membrane 894 and a semi-transparent orasure cassette 896, as they are placed or as they are relative to the reader 810. Conventional readers are used more to avoid operator errors and obtain data in the electronic format rather than to improve the sensitivity. In the implementation, however trans-visual (better than visual) sensitivity was obtained even in the reflection mode by virtue of ambient isolation and optimization of illumination, as described previously. A qualitative example 905 of trans-visual performance is shown in FIG. 9 where the reader is clearly able to detect a weak line invisible to the naked eye by using an image processing algorithm similar to conventional readers. An optimized image for all five RDTs used in this work is shown in FIG. 10. FIG. 10 shows exemplary (recorded and automatically processed) images of negative (bottom row 1015) and positive (top row 1025) tests for (a) Afla-V aflatoxin RDT, (b) Cardiac Panel RDT, (c) a custom hand held assay developed by ECBC (Edgewood Chemical Biological Center), (d) BioThreat Alert™ Anthrax RDT, and (e) Uni-Gold™ HIV RDT (Trinity Biotech).

Figure 11:
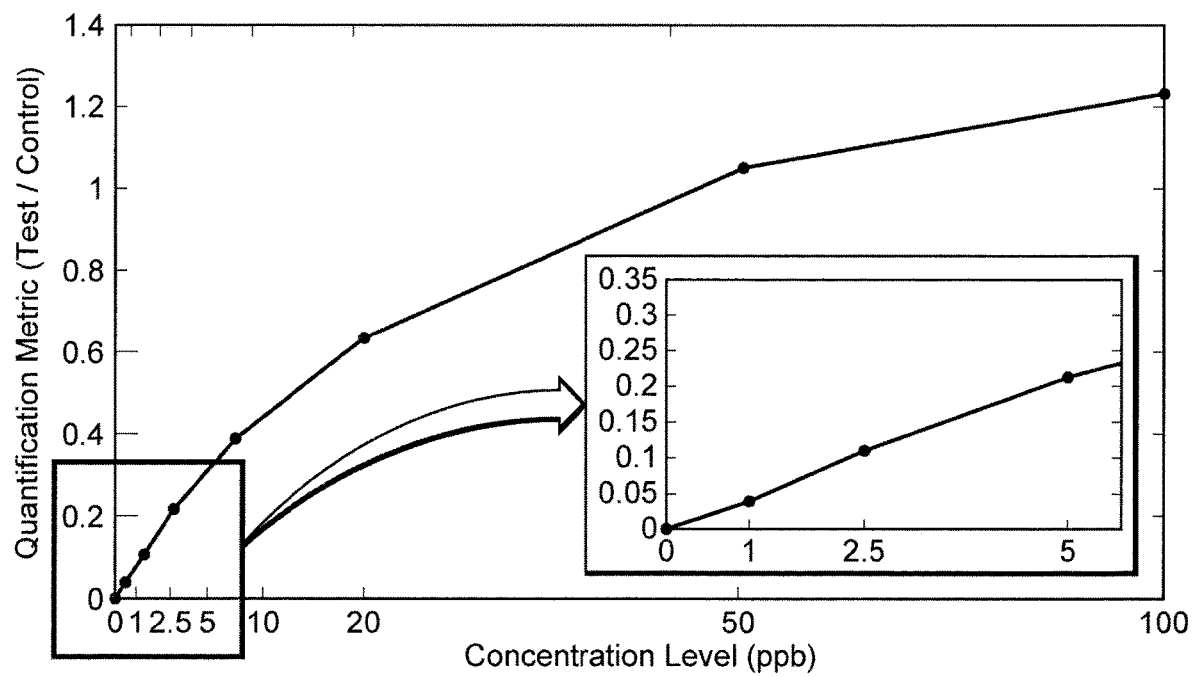
FIG. 11 shows the quantitative calibration curve for the Aflatoxin test that was generated using 160 different measurements is shown. For each concentration level, 2 different RDT were imaged 5 times.

To demonstrate the accuracy of this reader in the reflection mode, a statistically significant number of tests were performed on one high quality RDT cassette capable of quantitative performance, Afla-V aflatoxin RDT. The result is shown in FIG. 11. In reflection mode, in addition to the LEDs located on the PCB, cellphone flash can be used to illuminate the RDT under test.

Transmission mode readout was first proposed by Mudanyali et al[18] and qualitatively demonstrated to be an alternative to the reflection mode. However, their transmission mode required that both sides of the LFI strip be open and accessible to light-one side toward the illuminating source and the other side toward the camera- and this turned out to be a major impediment for practical use. The fact is that an overwhelming majority of RDT cassettes today on the market has only one open window for the strip with the other side being covered by a plastic back (for examples see FIGS. 4 and 5), thus precluding the use of the transmission mode except for a small number of specialized cassettes or cassettes custom designed for this mode.

The key insight that led to the contemplated embodiments disclosed herein is that nearly all RDT cassettes on the market are made of white or lightly colored plastic that is sufficiently translucent to allow sufficient light transmission through the cassette wall to provide adequate illumination of the LFI strip and ultimately detection by the camera. In addition, the translucent plastic acts as a diffuser substantially improving the uniformity of the strip illumination.

The advantages of these contemplated embodiments are summarized as follows:

The signal captured by the camera contains information about the density of gold particles throughout the thickness (3-dimensional morphology) of the paper strip rather than just on the surface or close to the surface, which will substantially increase the lower detectable limit compared with the reflection mode measurement.

Translucent plastic in the cassette wall in the pathway of light is generally strongly scattering and diffuses light which contributes to the uniformity of the illumination of the strip and this minimizes measurement errors.

The reflection mode illumination may cause multiple reflections from the RDT cassette, causing trouble in digital processing steps. This is particularly the case when the cassette window is covered with plastic, which is the prevailing situation with rapid tests used with saliva and which often also have weaker signal. The transmission mode avoids these problems.

Because of the above all light reaching the camera is diffused either through two layers of plastic with and without the strip or one layer plus the strip. Consequently the contrast over the camera field of view is considerably more uniform than for the reflection case as shown below, which reduces problems with camera saturation and white balance variation.

Figure 12:
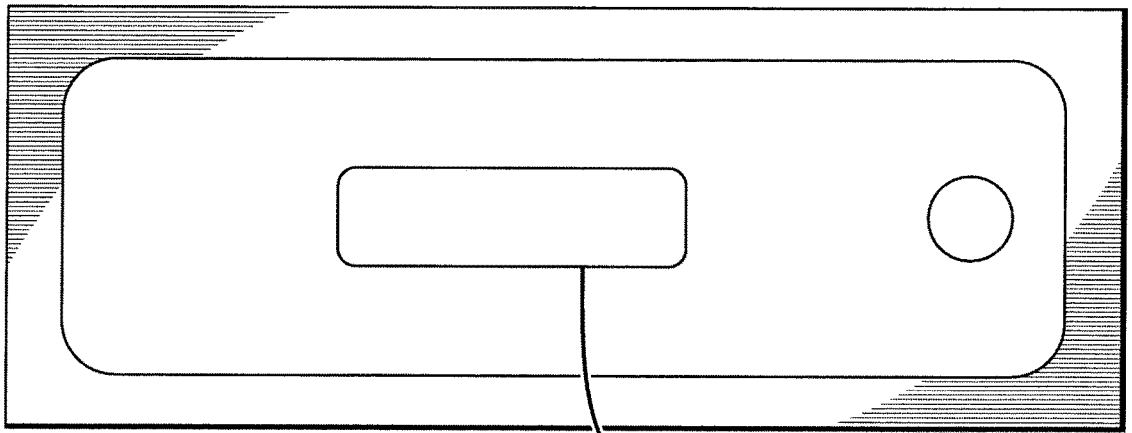
FIG. 12 shows the illumination pattern in the transmission mode

For the same reason as above, there are no shadows around the walls of the window (due to the oblique illumination angle of the light sources in reflection mode) which are also detrimental for the measurement. In fact, it was observed that the backside illumination creates a sharp edge 1245 around the window which may be beneficial in determination of the window position and line edges (FIG. 12)

Blank (not-activated) tests (RDTs or LFIs) have test and control bands. Antibodies or other chemicals that are necessary for the color changes are dispensed (e.g., injected or coated) to these bands and required for the successful operation. In transmission mode, these bands can be screened before the use as a quality control mechanism at the manufacturing side.

Figure 13:
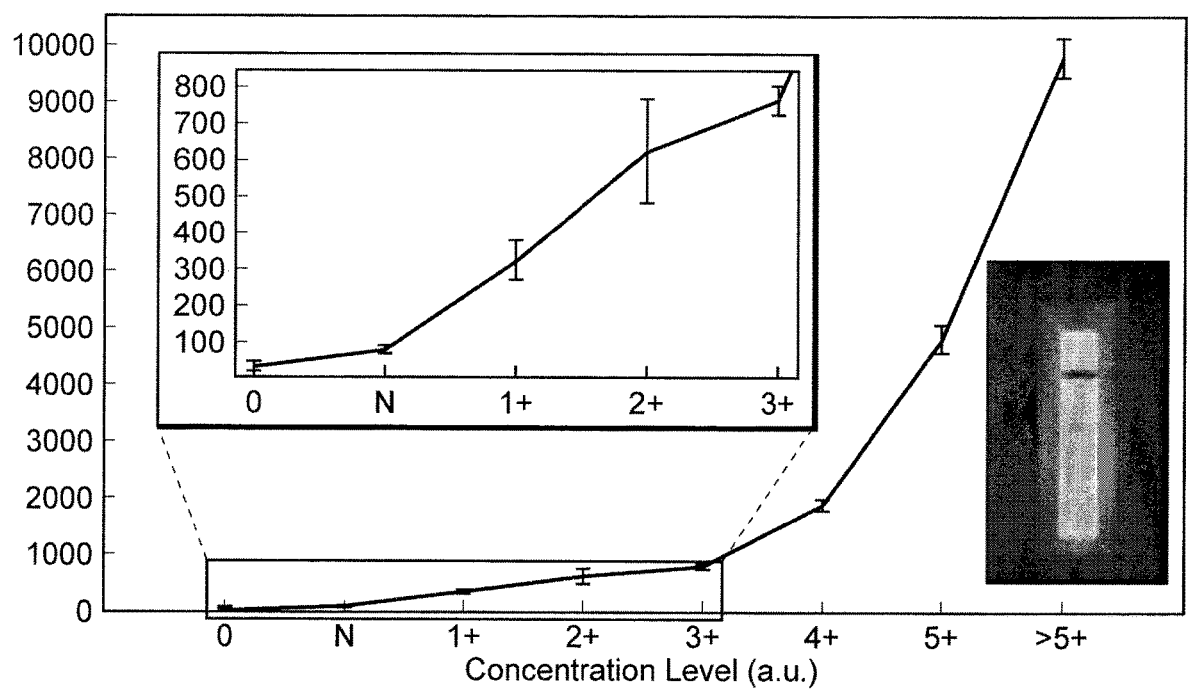
FIG. 13 shows the summary of our measurements on the dry standard Orasure RDT kits which represents various concentration levels ranging from blank (0) and negative (N) to high density levels (>5+). In the table below, the measurement intensity mean, standard deviation and CV values are shown together with the corresponding optical density levels provided by Orasure.

The performance of this transmission mode was confirmed using a set of calibration test RDTs from Orasure. The results are shown in FIG. 13. They confirm trans-visual sensitivity of <0.5% Optical Density and excellent CV of ~1%.

Figure 14:
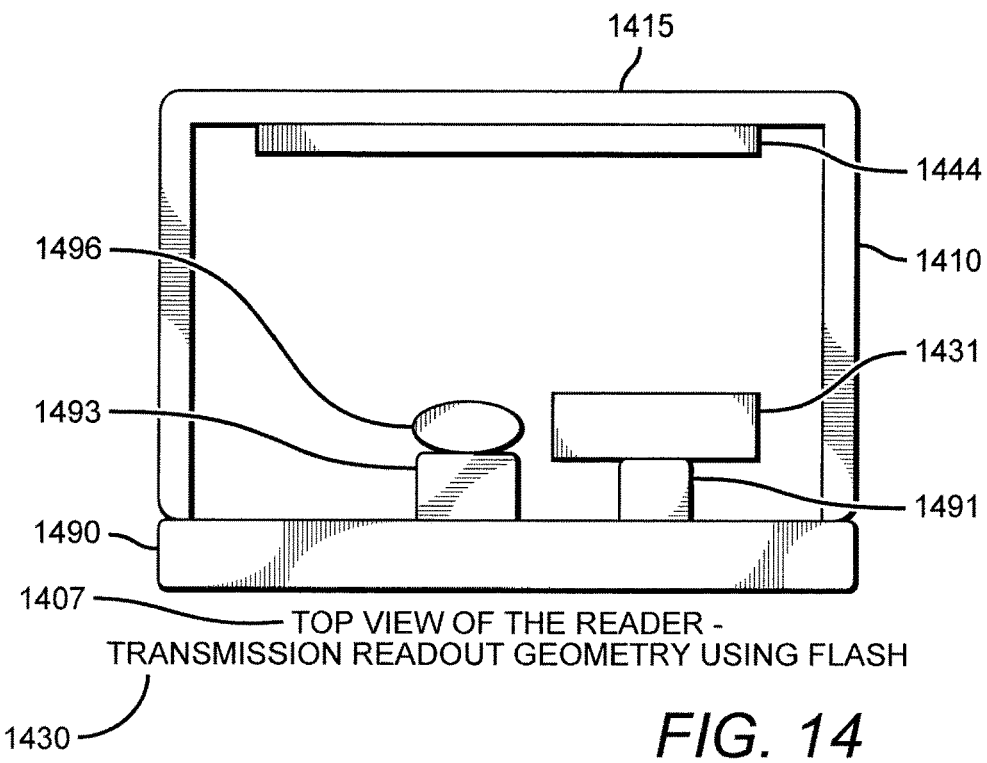
FIG. 14 shows the schematics for the transmission imaging/readout modality using the cell-phone flash and a mirror.

The transmission mode LEDs are located at the tray (behind the RDT under testing), and butt-coupled to the back of the plastic cassette. Moreover, instead of external LEDs, cell-phone flash can be used provided that a mirror is located at the tray. In this flash-transmission geometry, the RDT is located on the top of the flash and parallel to the cell-phone camera. The flash is controlled by the cell-phone application and illuminates the back of the cassette. The mirror located at the top of the tray reflects the image which is recorded via the cell-phone camera. See FIG. 14 for the transmission mode readout geometry using flash. In FIG. 14, the top view 1407 of a contemplated reader 1410 is shown in transmission readout geometry 1430, wherein the cell phone 1490 and the cell phone camera module 1493 is shown with an optional external lens 1496. The attachment point 1415 for the reader 1410 is shown, along with a mirror 1444 and the RDT 1431 near the cell phone flash 1491.

It should be emphasized that the all five imaging/readout capabilities described here, namely, (i) Reflection mode readout using the LEDs embedded on PCB, (ii) Reflection mode readout using cell-phone flash, (iii) Transmission mode readout using the LEDs embedded on the RDT tray (door), (iv) Transmission mode readout using the cell-phone flash with the use of a mirror and (v) Fluorescent mode readout using one or more LEDs on the PCB can be implemented on the same platform with minor or no mechanical adaptation or changes. The PCB has been designed to operate at any of the readout modes. Wirelessly controlling the PCB by sending flash pulses, the smartphone application allows the user to switch between readout modes or automatically chooses the readout mode based on the RDT type.

Smartphone Options

All of the currently-used, conventional reader implementations require multiple mechanical attachments that are physically customized to fit onto different smartphones, which may be acceptable for higher end professional markets, where users want to buy a complete reader instrument and are willing to pay for the cost of the smartphone in addition to the cost of the attachment, but it does limit the size of the addressable market and it is definitely too expensive for consumer markets. Different phones can be fitted on the same reader body by having adjustable rails or hooks but these tend to be clumsy, expensive, and they can be misadjusted through use.

Figure 15:
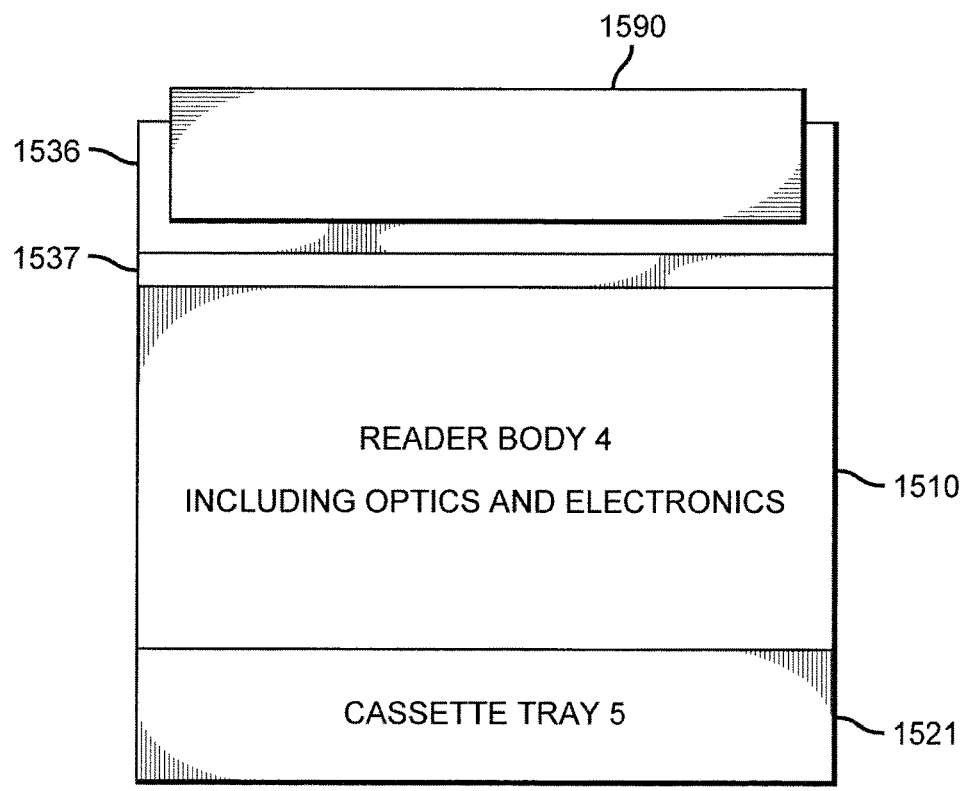
FIG. 15 shows universal reader design that can work with any smartphone or tablet, utilizing smartphone cases customized for each phone or tablet type.

Contemplated embodiments disclosed herein implement a low cost adaptation layer by using smartphone cases. These protective cases are very popular and sold in large quantities. Because of the huge volume, simple design, and little material they are very inexpensive ($10 to $30) and by definition they fit the smartphone 1590 perfectly. The architecture of this solution is shown FIG. 15. Case 2 1536 is affixed to the reader body 1510 via the attachment 3 1537. The cassette tray 5 1521 is also shown. This can be screws, glue, double sided tape, Velcro tape or another thin mechanical attachment or adaptor; each with its advantages or disadvantages but all feasible. The attachment would be permanent or semi permanent. It would initially be done in the factory and later maybe by the user.

Figure 16:
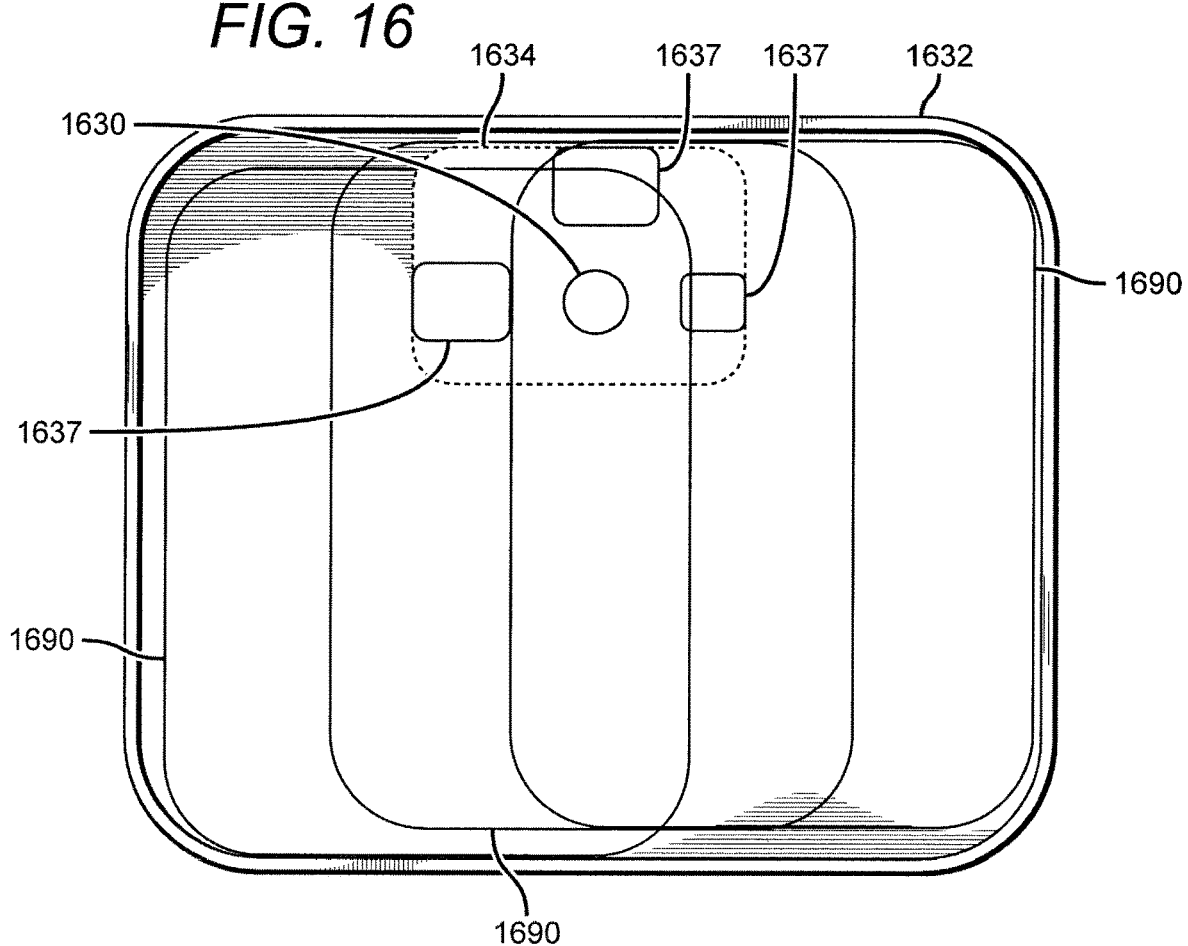
FIG. 16 shows that, by the optimized selection of the common location of flash/camera for various phones and tablets, the universal reader attachment can work with various smartphones and tablets.

With this arrangement reader body 4 can be the same for all smartphones and rapid tests and can be made inexpensively in large quantities with hard mold injection process but, in order to be universal, it has to be somewhat larger than any contemplated smartphone. The body 1632 must also have an opening on the top 1634 to accommodate different smartphones with different positioning of the camera 1630 relative to the main smartphone body 1690 and the flash 1637 relative to the camera 1630, which is shown in FIG. 16 in an exaggerated way to illustrate the point.

An alternative to the use of commercially available smartphone cases is to design a universal smartphone cradle by following the same principles as shown in FIGS. 7B and 7C, i.e. fixing the position of the smartphone in a cradle by the use of L-corner, springs, and slanted sides.

Auto-Focus Approach

The unique optical interface of the reader attachment was designed to uniformly illuminate the field-of-view of an area of larger than ~60 mm×~90 mm. This ensures that any rapid test cassette to be analyzed by this reader will be uniformly illuminated such that the reading variation caused by the illumination intensity is minimized, increasing the repeatability of measurements. On the other, the digital focusing of cell-phone camera is challenging during the image acquisition due to the need for most uniform illumination on the RDT plane that is located only ~20-60 mm from the cell-phone camera. Live RDT image consists of only spatial low-frequency components at this illumination configuration, often causing the camera's auto-focus algorithm to fail. For successful focusing by the camera, there should be significant amount of spatial high-frequency components (e.g., sharp edges and transitions or light oscillations) on the live image.

To help the camera achieve better optical focus, we first turn on the camera's flash in burst mode to create the amount of contrast necessary to achieve focusing on the image. This non-uniform short point source illumination provided by the flash generates the amount of contrast necessary for such focus algorithms.

Once the camera has focused on the image, we are able to preserve that focus distance throughout the test cycle by creating a class which implements the Android autofocus Callback interface and setting a Boolean flag upon successful focus. We are able to obtain the point source illumination from the camera's flash in order to improve our focus while still maintaining an even, single wavelength illumination for the image capture. Though our solution was designed to work with a contrast detection auto-focus system, it will improve focus distance detection for systems which use phase detection algorithms as well.

Illumination Control

Readers require sources of illumination and associated control electronics and battery housed outside the smartphone. In Mudanyali's reader [18], the control is provided by the software application in the smartphone via a cable which plugs into the smartphone micro USB power connector. However, many smartphones do not have the capability for outbound control through their power connector. On the other hand all smartphones have an audio jack which can be used to transmit control via an audio signal. Both approaches work but they do require external cabling and connectors that add to the cost and reduce reliability.

Figure 17:
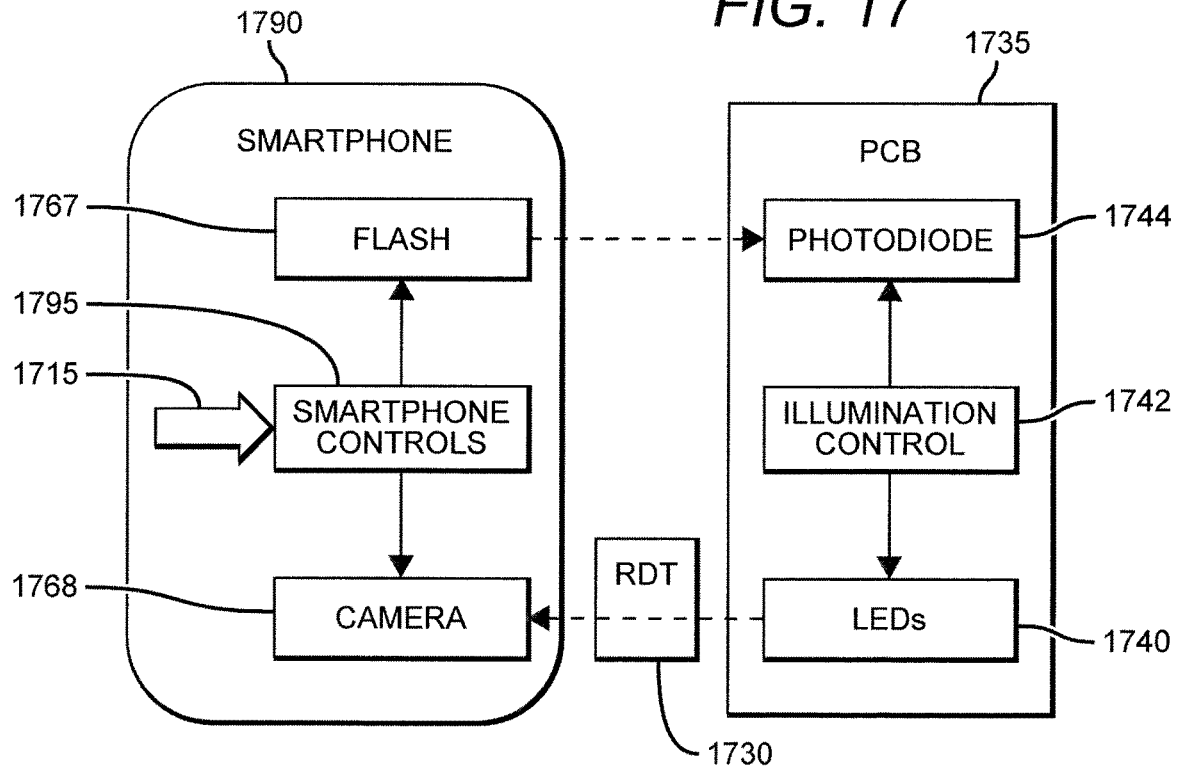
FIG. 17 describes the communication between the smartphone and tablet (application) and the embedded PCB. The reader application running on the smartphone or tablet can control the flash pulses generated by the camera and control the electronics on the PCB.

Contemplated embodiments provide a wireless control connection via RF signals, including Bluetooth, WiFi, and Near Field Communications (NFC), or using an optical signal generated by the flash in the smartphone 1790. The block diagram of this approach is shown in FIG. 17. Upon users' command to initiate the test 1715, the software (not shown) application generates an Android command that switches the flash 1767 on. The burst of the flash light (not shown) is detected by a photo sensor (diode or transistor) 1744 that is located on the PCB 1735, wherein the photo sensor 1744 triggers the illumination control electronics 1742 to activate the LEDs 1740 for RDT 1730 illumination. A single burst is sufficient for the usual operation where the illumination parameters are fixed and only the timing needs to be controlled; if more complex control is desired (i.e. choice of LEDs, light level, or illumination duration), the flash 1767 can be commanded to generate a sequence of bursts that can be appropriately decoded by the illumination control 1742. Note that this optical control method not only avoids any external cables but it is also considerably less expensive than other wireless methods that might be considered. In summary, in contemplated platforms, the flash can be used for reflection and transmission mode illumination of RDTs as well as the wireless control of the reader attachment by the cell-phone application.

REFERENCES

The following references are referred to herein by their reference number. These references are incorporated herein in their entirety by reference.

1 P. Yager, T. Edwards, E. Fu, K. Helton, K. Nelson, M. R. Tam and B. H. Weigl, *Nature,* 2006, 442, 412-418.

2 S. Banoo, D. Bell, P. Bossuyt, A. Herring, D. Mabey, et al., Nat Rev Microbio, 2006, 4, 21-31.

3 M. Dhorda, P. Piola, D. Nyehangane, B. Tumwebaze, A. Nalusaji, C. Nabasumba, E. Turyakira, R. McGready, E. Ashley, P. J. Guerin, G. Snounou, *Am J Trop Med Hyg,* 2012, 86(1), 93-95.

4 I. N. Okeke, R. W. Peeling, H. Goossens, R. Auckenthaler, S. S. Olmsted, J. F. de Lavison, B. L. Zimmer, M. D. Perkins, and K. Nordqvist, *Drug Resist Updat,* 2011, 14(2), 95-106.

5 C. Drakeley and H. Reyburn, *Trans R Soc Trop Med Hyg,* 2009, 103(4), 333-337.

6 C. K. Murray, R. A. Gasser Jr, A. J. Magill, and R. S. Miller, *Clin Microbiol Rev,* 2008, 21(1), 97-110.

7 J. Skarbinski, P. O. Ouma, L. M. Causer, S. K. Kariuki, J. W. Barnwell, J. A. Alaii, A. M. de Oliveira, D. Zurovac, B. A. Larson, R. W. Snow, A. K. Rowe, K. F. Laserson, W. S. Akhwale, L. Slutsker, and M. J. Hamel, *Am J Trop Med Hyg,* 2009, 80(6), 919-926.

8 L. A Mills, J. Kagaayi, J. P. Shoff, K. Newell, J. B. Bwanika, V. Ssempijja, S. Aluma, T. C. Quinn, S. J. Reynolds, R. H. Gray, *Trans R Soc Trop Med Hyg,* 2010, 104(3), 237-239.

9 http://www.itu.int/ITU-D/ict/publications/idi/material/2012/MIS2012_highlights_short.pdf, Retrieved on 12.25.2012.

10 H. Zhu, O. Yaglidere, T. Su, D. Tseng, and A. Ozcan, *Lab Chip,* 2011, 11, 315-322.

11 D. Tseng, O. Mudanyali, C. Oztoprak, S. O. lsikman, I. Sencan, O. Yaglidere, and A. Ozcan, Lab Chip, 2010, 10, 1787-1792.

12 O. Mudanyali, D. Tseng, C. Oh, S. O. lsikman, I. Sencan, W. Bishara, C. Oztoprak, S. Seo, B. Khademhosseini, and A. Ozcan, Lab Chip, 2010, 10, 1417-1428.

13 G. McKiernan, *Searcher,* 2010, 18 (3), 48-51.

14 A. W. Martinez, S. T. Philips, E. Carrilho, S. W. Thomas III, Hayat Sindi and G. M. Whitesides, *Anal Chem,* 2008, 80, 3699-3707.

15 Adler R., *Health Care Unplugged: The Evolving Role of Wireless Technology*, California HealthCare Foundation, 2007

16. A. Coskun, J. Wong, D. Khodadadi, R. Nagi, A. Tey, and A. Ozcan, *Lab Chip,* 2012, DOI: 10.1039/C2LC41152K.

17 http://www.idc.com/qetdoc.jsp?containerId=prUS23771812.

18 O. Mudanyali, S. Dimitrov, U. Sikora, S. Padmanabhan, I. Navruz and A. Ozcan, *Lab Chip,* 2012, 12, 2678-2686.

19 http://holomic.com/content/2012/07/01/holomic-introduces-a-smartphone-based-rapid-test-reader-at-aacc-2012/ Introduction of rapid reader

20 PCT/US2012/040282

21 Faulstich et al in "lateral Flow Imunoassay, Edited by Raphael Wong and Harley Tse, Springer 2009.

22 http://www.qiagen.com/about-us/contact/oem-services/ese-instruments/esequant-lateral-flow-system, Retrieved on 12.31.2013.

23 US2013/0244339

Thus, specific embodiments and methods of a universal smartphone-based rapid diagnostic test reader with transvisual sensitivity have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the specification and claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. A universal rapid diagnostics test reader, comprising:
    a set of control electronics, wherein the set of control electronics comprise processor electronics that control an illumination component;
    a smartphone, wherein the smartphone comprises a wireless communication component;
    a digital camera component, wherein the digital camera component is operatively located in the smartphone, wherein the wireless communication component comprises a wireless connection that is operatively initiated and engaged by a flash in the digital camera component and a photo-detector in the set of control electronics, and wherein the flash controls an illumination component;
    an illumination component, wherein the illumination component comprises at least one light-emitting diode and a transmission mode of operation where the rapid diagnostic test is located between the light-emitting diode and the camera component;
    a housing component, and
    a single rapid diagnostics universal test tray comprising a series of cradles formed by ridges at different heights, orientations, and lateral extensions, wherein the single tray can hold at least two different types or kinds of rapid diagnostics test having a shape and a size in a fixed position relative to the digital camera component and the illumination component, wherein the single tray can only hold one test at one time, and wherein the single rapid diagnostics universal test tray can accommodate different types or kinds of rapid diagnostics tests in the same universal test tray without additional mechanical adaptation to each test before it is placed in the tray, without a mechanical adapter surrounding each test before it is placed in the rapid diagnostics universal test tray, or without additional mechanical components applied to each test before it is placed in the rapid diagnostics universal test tray.

2. The universal rapid diagnostics test reader of claim 1, wherein the digital camera component comprises at least one lens, at least one image sensor, at least one analog to digital converter, at least one digital image processor, at least one flash, at least one microprocessor or a combination thereof.

3. The universal rapid diagnostics test reader of claim 1, wherein the digital camera component uses autofocus and wherein the illumination component comprises flash illumination.

4. The universal rapid diagnostics test reader of claim 1, wherein the wireless communication component comprises a wireless connection that is operatively initiated and engaged by non-optical functions.

5. The universal rapid diagnostics test reader of claim 4, wherein non-optical functions comprise WIFI, IEEE standard Bluetooth, or Near Field Communications.

6. The universal rapid diagnostics test reader of claim 1, wherein the flash controls light-emitting diode selection.

7. The universal rapid diagnostics test reader of claim 1, wherein the smartphone is enclosed in its case before being operatively engaged with the housing component.

8. The universal rapid diagnostics test reader of claim 1, wherein the smartphone is operatively engaged with the housing component.

9. The universal rapid diagnostics test reader of claim 8, wherein the smartphone is further constrained with an L-shaped corner component.

10. The universal rapid diagnostics test reader of claim 8, wherein the smartphone is held in a fixed position in a planar direction with at least one spring.

11. The universal rapid diagnostics test reader of claim 8, wherein the smartphone is constrained in a perpendicular direction with a slanted side or a curved side.

12. The universal rapid diagnostics test reader of claim 1, wherein the illumination component includes illumination of rapid diagnostics test by one or more light emitting diodes at the wavelength of imaging for chromatographic rapid diagnostic tests or at the excitation wavelength for the fluorescent rapid diagnostic tests.

13. The universal rapid diagnostics test reader of claim 12, wherein the illumination component comprises a reflection mode of operation where one or more light-emitting diodes and the camera component that are on a front side of the rapid diagnostic test with the light-emitting diode axis that is roughly perpendicular to the rapid diagnostic test plane.

14. The universal rapid diagnostics test reader of claim 13, wherein the light-emitting diode is the flash light-emitting diode that is part of the camera component illuminating a strip on the rapid diagnostics test from the front side.

15. The universal rapid diagnostics test reader of claim 1, wherein the rapid diagnostic test may comprise a bare strip, a strip on a translucent plastic backing, a conventional strip packaged in a translucent plastic cassette or a combination thereof.

16. The universal rapid diagnostics test reader of claim 1, wherein the light-emitting diode is the flash light-emitting diode that is a part of the camera component.

17. The universal rapid diagnostics test reader of claim 16, wherein the camera is imaging a strip via a mirror placed in front of the rapid diagnostics test.

18. The universal rapid diagnostics test reader of claim 1, wherein the housing component is designed to enclose all components of the reader into a light tight enclosure and wherein the rapid diagnostic test is illuminated only by the illumination from the reader and not illuminated by ambient light.

19. The universal rapid diagnostics test reader of claim 1, wherein the rapid diagnostics tray secures a rapid diagnostics test in the tray with an L-shaped corner component.

20. The universal rapid diagnostics test reader of claim 1, wherein the rapid diagnostic test is held in a fixed position in a planar direction with at least one spring.

21. The universal rapid diagnostics test reader of claim 1, wherein the rapid diagnostic test is constrained in a perpendicular direction with a slanted side or a curved side.

22. The universal rapid diagnostics test reader of claim 1, wherein the more than one rapid diagnostic tests are constrained in their position by their own cradles and posts customized on the same tray.

* * * * *